US010829420B2

(12) United States Patent
Ren et al.

(10) Patent No.: US 10,829,420 B2
(45) Date of Patent: Nov. 10, 2020

(54) FILAMENTOUS ORGANISM-DERIVED CARBON-BASED MATERIALS, AND METHODS OF MAKING AND USING SAME

(71) Applicants: THE REGENTS OF THE UNIVERSITY OF COLORADO, A BODY CORPORATE, Denver, CO (US); The Government of the United States of America, as represented by the Secretary of the Navy, Washington, DC (US)

(72) Inventors: Zhiyong Ren, Superior, CO (US); Mitchell Tyler Huggins, Boulder, CO (US); Justin C. Biffinger, Dayton, OH (US); Corey T. Love, Alexandria, VA (US); Se-Hee Lee, Superior, CO (US); Justin M. Whiteley, Chicago, IL (US)

(73) Assignees: The Regents of the University of Colorado, a body corporate, Denver, CO (US); The Government of the United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 16/319,734

(22) PCT Filed: Jul. 21, 2017

(86) PCT No.: PCT/US2017/043304
§ 371 (c)(1),
(2) Date: Jan. 22, 2019

(87) PCT Pub. No.: WO2018/075112
PCT Pub. Date: Apr. 26, 2018

(65) Prior Publication Data
US 2019/0270677 A1 Sep. 5, 2019

Related U.S. Application Data

(60) Provisional application No. 62/365,515, filed on Jul. 22, 2016, provisional application No. 62/365,536, filed on Jul. 22, 2016.

(51) Int. Cl.
*C04B 35/83* (2006.01)
*C04B 35/626* (2006.01)
(Continued)

(52) U.S. Cl.
CPC .............. *C04B 35/83* (2013.01); *C01B 32/00* (2017.08); *C01B 32/20* (2017.08);
(Continued)

(58) Field of Classification Search
CPC ... C04B 35/83; C04B 35/62655; C04B 35/64; C04B 2235/3275; C04B 2235/3418;
(Continued)

(56) References Cited

U.S. PATENT DOCUMENTS 2,083,303 A 6/1937 Krezil et al.
2,508,474 A 5/1950 Slyh et al.
(Continued)

FOREIGN PATENT DOCUMENTS

CN 103641113 A 3/2014
EP 0490317 A1 6/1992
EP 3095514 A1 11/2016

OTHER PUBLICATIONS

PCT International Search Report & Written Opinion dated Apr. 3, 2018 for PCT International Patent Application No. PCT/US2017/043304.

*Primary Examiner* — Daniel C. McCracken
(74) *Attorney, Agent, or Firm* — Saul Ewing Arnstein & Lehr LLP; Kathryn Doyle; Domingos J. Silva

(57) ABSTRACT

The invention provides filamentous organism-derived carbonaceous materials doped with organic and/or inorganic
(Continued)

compounds, and methods of making the same. In certain embodiments, these carbonaceous materials are used as electrodes in solid state batteries and/or lithium-ion batteries. In another aspect, these carbonaceous materials are used as a catalyst, catalyst support, adsorbent, filter and/or other carbon-based material or adsorbent. In yet another aspect, the invention provides battery devices incorporating the carbonaceous electrode materials.

12 Claims, 18 Drawing Sheets

(51) Int. Cl.
| | |
|---|---|
| *C04B 35/64* | (2006.01) |
| *C12P 1/02* | (2006.01) |
| *H01M 4/587* | (2010.01) |
| *H01M 10/0525* | (2010.01) |
| *H01M 10/0562* | (2010.01) |
| *H01M 10/0568* | (2010.01) |
| *H01G 11/44* | (2013.01) |
| *H01G 11/34* | (2013.01) |
| *H01G 11/40* | (2013.01) |
| *H01G 11/32* | (2013.01) |
| *H01G 11/26* | (2013.01) |
| *H01M 4/1393* | (2010.01) |
| *C01B 32/20* | (2017.01) |
| *H01G 11/24* | (2013.01) |
| *H01M 4/133* | (2010.01) |
| *C01B 32/00* | (2017.01) |
| *H01M 4/02* | (2006.01) |
| *H01M 4/36* | (2006.01) |

(52) U.S. Cl.
CPC ........ *C04B 35/62655* (2013.01); *C04B 35/64* (2013.01); *C12P 1/02* (2013.01); *H01G 11/24* (2013.01); *H01G 11/26* (2013.01); *H01G 11/32* (2013.01); *H01G 11/34* (2013.01); *H01G 11/40* (2013.01); *H01G 11/44* (2013.01); *H01M 4/02* (2013.01); *H01M 4/133* (2013.01); *H01M 4/1393* (2013.01); *H01M 4/362* (2013.01); *H01M 4/587* (2013.01); *H01M 10/0525* (2013.01); *H01M 10/0562* (2013.01); *H01M 10/0568* (2013.01); C04B 2235/3275 (2013.01); C04B 2235/3418 (2013.01); C04B 2235/422 (2013.01); C04B 2235/428 (2013.01); C04B 2235/5248 (2013.01); C04B 2235/604 (2013.01); C04B 2235/606 (2013.01); C04B 2235/6562 (2013.01); C04B 2235/6567 (2013.01); *H01M 2300/0037* (2013.01); H01M 2300/0068 (2013.01)

(58) Field of Classification Search
CPC ........ C04B 2235/422; C04B 2235/428; C04B 2235/5248; C04B 2235/604; C04B 2235/606; C04B 2235/6562; C04B 2235/6567; H01G 11/44; H01G 11/34; H01G 11/40; H01G 11/32; H01G 11/26; H01G 11/24; H01M 4/1393; H01M 4/133; H01M 4/02; H01M 4/362; H01M 4/587; H01M 10/0525; H01M 10/0562; H01M 10/0568; H01M 2300/0037; H01M 2300/0068; C01B 32/20; C01B 32/00; C12P 1/02
See application file for complete search history.

(56) References Cited

U.S. PATENT DOCUMENTS

| | | |
|---|---|---|
| 3,427,120 A | 2/1969 | Shindo et al. |
| 3,903,268 A | 9/1975 | Balassa |
| 4,699,896 A | 10/1987 | Freeman et al. |
| 5,204,310 A | 4/1993 | Tolles et al. |
| 5,298,313 A | 3/1994 | O'Brien et al. |
| 5,465,023 A * | 11/1995 | Garner ................. F03H 1/0043 313/293 |
| 5,521,008 A | 5/1996 | Gorokhov et al. |
| 2005/0281730 A1* | 12/2005 | Theriault ............ C04B 38/0054 423/448 |
| 2006/0111007 A1 | 5/2006 | Escaffre et al. |
| 2010/0196994 A1 | 8/2010 | Van Leeuwen et al. |
| 2011/0183180 A1* | 7/2011 | Yu ......................... H01M 4/382 429/128 |
| 2012/0122164 A1 | 5/2012 | El-Shafie |
| 2012/0282446 A1 | 11/2012 | Jo et al. |
| 2013/0334468 A1 | 12/2013 | Taniguchi et al. |
| 2014/0113200 A1 | 4/2014 | Seymour |

* cited by examiner

FIG. 2A
FIG. 2B
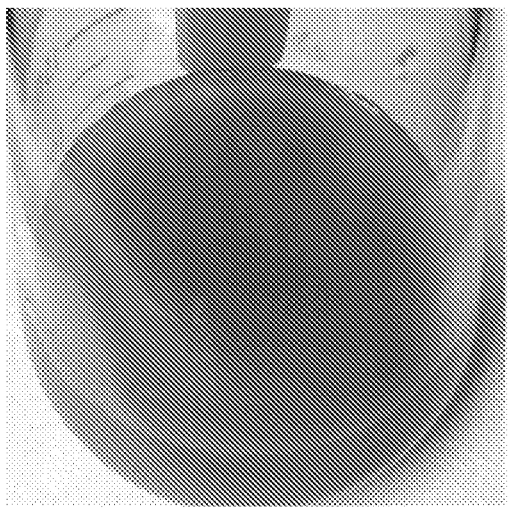
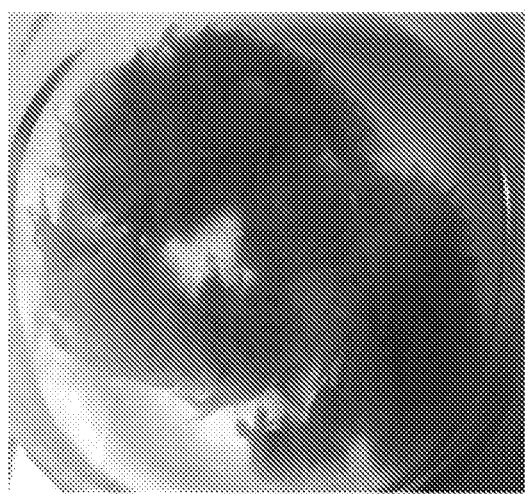
FIG. 2C
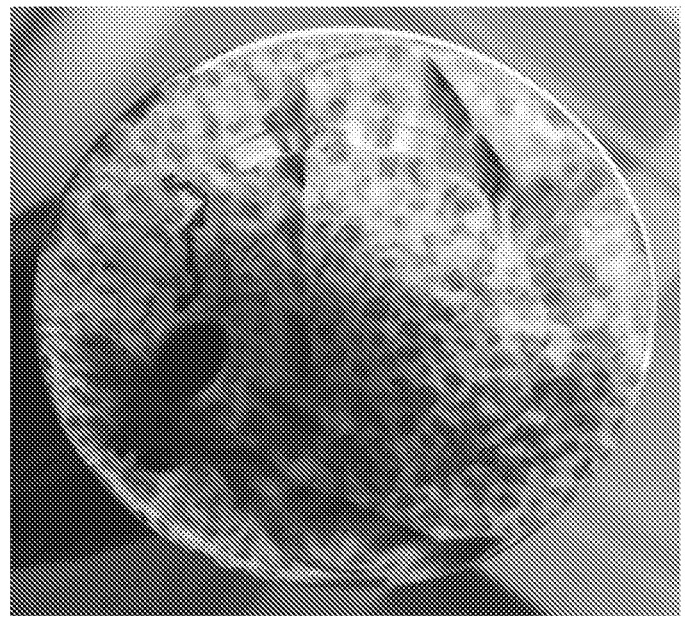

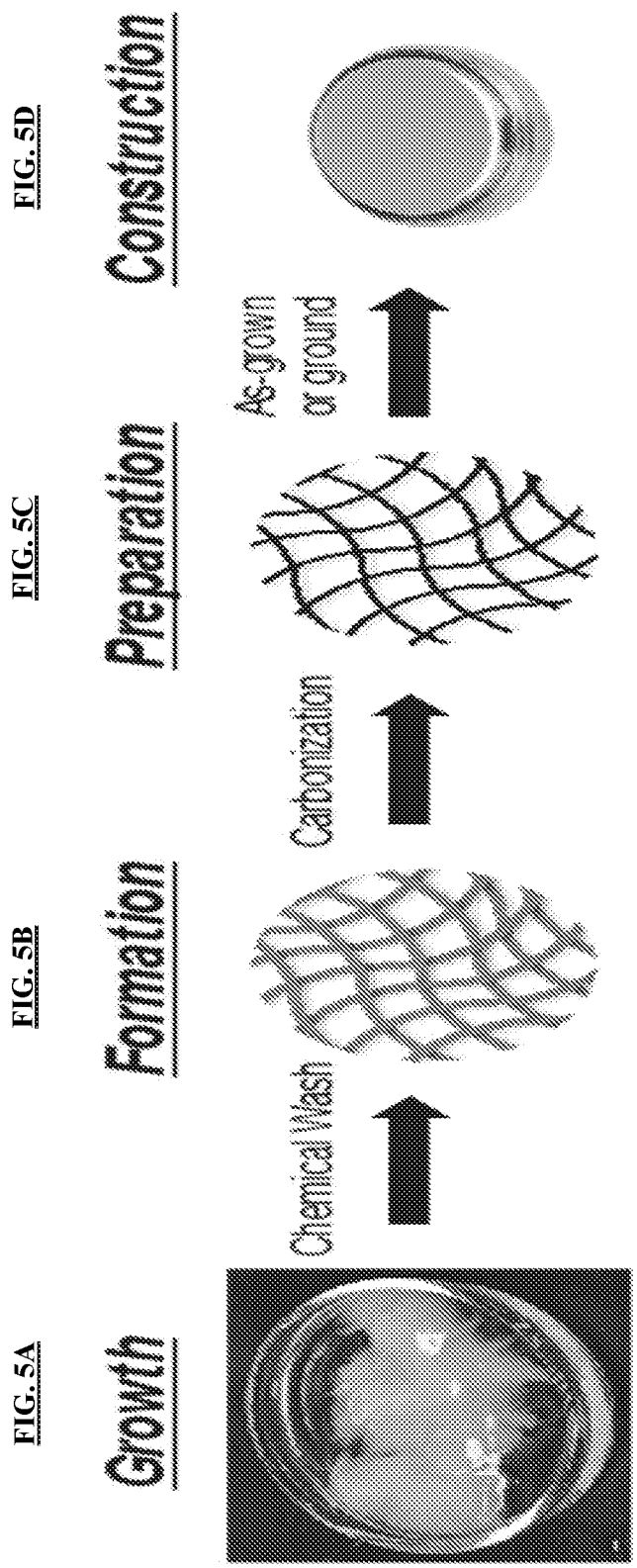

FILAMENTOUS ORGANISM-DERIVED CARBON-BASED MATERIALS, AND METHODS OF MAKING AND USING SAME

CROSS-REFERENCE TO RELATED APPLICATIONS

The present application is a 35 U.S.C. § 371 national phase application of, and claims priority to, International Application No. PCT/US2017/043304, filed Jul. 21, 2017, which claims priority under 35 U.S.C. § 119(e) to U.S. Provisional Applications No. 62/365,515, filed Jul. 22, 2016, and No. 62/365,536, filed Jul. 22, 2016, all of which applications are incorporated herein by reference in their-entireties.

STATEMENT REGARDING FEDERALLY SPONSORED RESEARCH OR DEVELOPMENT

This invention was made with government support under grant numbers N00014-15-1-2065 awarded by the Office of Naval Research and N00014-12-1-0293 awarded by the U.S. Naval Research Laboratory. The government has certain rights in the invention.

BACKGROUND OF THE INVENTION

Carbon is an ubiquitous material that is widely used in medicine, engineering and materials science. Carbon can exist in a multitude of forms, and can be tailored to possess various properties that may be required for a specific application. The list of application includes aircraft brakes, high temperature molds, rocket nozzles and exit cones, tires, ink, nuclear reactors, fuel particles, filters, prosthetics, fuel cells, airplanes and sporting equipment. In particular, the use of sophisticated carbon architecture, such as carbon nanotubes (CNT), and the doping of carbons with various atoms has been a highly studied area in materials science research. For example, carbonaceous materials are ideal surfaces for mounting active catalytic compounds such as transition metals as the highly porous structure of carbon materials allows for high surface areas in a relatively small volume. Additionally, the porous nature of the materials makes carbonaceous materials ideal adsorbents.

Energy storage is a trillion-dollar industry, in both production and hazardous waste disposal, servicing every facet of modern society. With the rapid adoption of consumer electronics and electric vehicles, and with the growing need for renewable energy storage, the demand for battery performance is dramatically increasing. The next generation battery technologies are predicted to utilize advancements in nanotechnology and material chemistries. In particular, the use of sophisticated carbon architecture for anodes, such as carbon nanotubes (CNT), and the doping of carbons with various heteroatoms (e.g., N, P, B, and Si) and transition metal nanoparticles (e.g., Co, Fe, and Mn), has been a highly studied area in battery research. Advancements in material processing have been paramount in improving power densities, but often come with increased cost, energy, and resource disadvantages. In fact, for every kWh produced by a modern Li-ion battery, more than 400 kWh is required. Further, an additional 3 order of magnitude improvement is needed for CNT manufacturing to achieve a break-even environmental impact comparable to modern graphite based anodes. If future battery technologies are to truly aid in the progression of modern society, materials with greatly improved performance must be efficiently manufactured using a sustainable feedstock.

There is a need in the art for novel carbon-based materials and methods of producing them. In certain embodiments, these materials need to be manufactured from sustainable, environmentally friendly feedstock. In other embodiments, the methods of manufacturing these novel carbon-based materials should be flexible and adaptable in order to incorporate the doping of various non-carbon atoms in order to manipulate the material's properties. There is also a need in the art for novel electrode materials and methods of producing them. In certain embodiments, these novel carbon-based electrode materials should be carbon-based and manufactured from sustainable, environmentally friendly feedstock. In other embodiments, the methods of manufacturing these novel carbon-based electrode materials should be flexible and adaptable in order to allow for manipulating the material's properties. The present invention addresses and meets these needs.

BRIEF SUMMARY OF THE INVENTION

The invention provides a carbonaceous material comprising a graphitic, partially graphitic, or amorphous carbon matrix, wherein the carbon matrix comprises a plurality of fibers. The invention further provides a battery device comprising at least one carbonaceous material of the invention and a lithium-containing electrolyte. The invention further provides a method of producing a carbonaceous material comprising a graphitic carbon matrix.

In certain embodiments, each one of the plurality of fibers independently has a diameter ranging from about 0.1 μm to about 100 μm and is in physical contact with at least one other of the plurality of fibers. In other embodiments, the carbon matrix has a surface area ranging from about 1 $m^2$ $g^{-1}$ to about 3,000 $m^2$ $g^{-1}$. In yet other embodiments, the carbon matrix comprises a plurality of pores that are present throughout the carbon matrix. In yet other embodiments, each one of the plurality of pores independently has a diameter ranging from about 0.1 μm to about 1 cm and is in fluid connection with at least one other of the plurality of pores. In yet other embodiments, the volumetric density of the material range between about 0.01 $g/cm^3$ to about 2.2 $g/cm^3$.

In certain embodiments, the material is prepared by carbonizing a filamentous organism optionally grown in the presence of at least one organic and/or inorganic compound wherein, if present, at least a portion of the at least one organic and/or inorganic compound is within or on the surface of the carbon matrix.

In certain embodiments, the filamentous organism is at least one selected from the group consisting of a filamentous algae, filamentous fungus and filamentous bacterium. In other embodiments, the filamentous organism is wild type or genetically modified *Neurospora crassa*.

In certain embodiments, at least one of the plurality of fibers is not physically bound to any of the others of the plurality of fibers. In other embodiments, at least one of the plurality of fibers is physically bound to at least one other of the plurality of fibers. In yet other embodiments, at least one of the plurality of fibers is physically bound to a first other of the plurality of fibers through a first branching point and physically bound to a second other of the plurality of fibers through a second branching point, wherein the separation of the first and second branching points along the length of the at least one of the plurality of fibers ranges from about 0.1 μm to about 1000 μm.

In certain embodiments, the carbon matrix further comprises at least one organic and/or inorganic compound that is within and/or on the surface of at least a fraction of the plurality of fibers and is present throughout the carbon matrix. In other embodiments, the at least one inorganic compound is selected from the group consisting of transition metal salts, alkali metal salts, alkaline earth metal salts, nitrate salts, sulfate salts, phosphate salts, metal particles, metalloid particles, metal oxides. In yet other embodiments, the at least one inorganic compound is selected from the group consisting of cobalt nitrate, sodium nitrate, magnesium sulfate and silicon nanoparticles.

In certain embodiments, the filamentous organism is carbonized by heating to a maximum temperature of about 100° C. to about 2,500° C. In other embodiments, the filamentous organism is heated from room temperature to the maximum temperature at a rate of about 1° C./min to about 100° C./min. In yet other embodiments, the filamentous organism is heated at the maximum temperature for about 1 hours to 100 hours. In yet other embodiments, the filamentous organism is heated in the presence of a gas with a flow rate between about 1 mL/min and about 1000 mL/min. In yet other embodiments, the filamentous organism is heated in a vacuum.

In certain embodiments, each one of the plurality of pores independently has a diameter ranging from about 1 μm to about 10 mm.

In certain embodiments, the material further comprises a compound selected from silicon nanoparticles, silicon oxide nanoparticles and $Co_2O_3$ nanoparticles. In other embodiments, the material is suitable for use as an electrode. In yet other embodiments, the material is suitable for use as an electrode in a solid state battery or a lithium-ion battery.

In certain embodiments, the method comprises carbonizing a dried organic material comprising a filamentous organism. In other embodiments, the dried organic material is shaped or pressed. In yet other embodiments, the dried organic material comprises a binding material and/or is in powder form.

In certain embodiments, the method further comprises drying, and/or flash freezing and lyophilizing, a filamentous organism, so as to form the dried organic material.

In certain embodiments, the filamentous organism is grown in a medium under light. In other embodiments, the filamentous organism is grown in the presence of at least one organic and/or inorganic compound. In yet other embodiments, the filamentous organism is at least one selected from the group consisting of a filamentous algae, filamentous fungus and filamentous bacterium. In yet other embodiments, the filamentous organism is wild type or genetically modified *Neurospora crassa*. In yet other embodiments, the filamentous organism is grown for a period of time of about 1 to about 5 days. In yet other embodiments, the medium is wastewater. In yet other embodiments, the wastewater comprises at least one selected from the group consisting of biological matter, organic waste, transition metal salts, heavy metal salts, inorganic nanoparticles and metal oxides. In yet other embodiments, the at least one inorganic compound is selected from the group consisting of cobalt salts, sodium salts, magnesium salts, nickel salts, zinc salts, manganese salts, iron salts and silicon particles. In yet other embodiments, the at least one inorganic compound is selected from the group consisting of cobalt nitrate, sodium nitrate, ammonium nitrate, magnesium sulfate and silicon nanoparticles.

In certain embodiments, the filamentous fungus is dried by a method selected from the group consisting of lyophilization and low-heat drying.

In certain embodiments, the dried organic material is carbonized by heating at a rate of about 20° C./min from room temperature to a maximum temperature of about 800° C. In other embodiments, the dried organic material is heated at the maximum temperature for about 2 hours. In yet other embodiments, the dried organic material is heated in the presence of a gas selected from the group consisting of $N_2$, $NH_3$, argon, $H_2S$ and air. In yet other embodiments, the dried organic material is heated in the presence of nitrogen gas with a flow rate between about 10 mL/min and about 100 mL/min. In yet other embodiments, the shaped dried organic material is contacted with a conductive wire before carbonization.

BRIEF DESCRIPTION OF THE DRAWINGS

The following detailed description of specific embodiments of the invention will be better understood when read in conjunction with the appended drawings. For the purpose of illustrating the invention, specific embodiments are shown in the drawings. It should be understood, however, that the invention is not limited to the precise arrangements and instrumentalities of the embodiments shown in the drawings.

FIG. 1A illustrates a starting feedstock of filamentous fungus. FIG. 1B illustrates a sequence wherein filamentous microorganisms are washed, dried, optionally compressed, optionally ground, and optionally mixed with a binder.

FIG. 1C represents a sequence wherein the fungus is heated and carbonized.

FIGS. 2A-2C comprise photographs depicting the progress of fungal growth in a growth medium. FIG. 2A is a photograph of silicon nanoparticles suspended in a growth medium. FIG. 2B illustrates adsorption of silicon on the growing fungal biomass. FIG. 2C illustrates full encapsulation of cathode material by the growth of the fungal biomass.

FIG. 4A depicts fungi growth in municipal wastewater. FIG. 4B depicts fungi growth in brewery wastewater. FIG. 4C depicts fungi growth in iron sludge residue from a drinking water filtration plant.

FIGS. 5A-5D comprise schematics of a process of integrating fungal derived structures into a battery. The fungal derived structures can integrate battery materials such as silicon, tin, sulfur, manganese and high voltage cathode materials. FIG. 5A depicts a fungus being grown in a particular growth medium and environment. FIG. 5B illustrates that, following a chemical wash dependent on the material being used, the fungus is formed into any geometry that may be needed. For coin cell cases, the material is formed into a ½" punch. FIG. 5C illustrates that a carbonization process occurs in which the biomass is removed and graphitic carbon is left. FIG. 5D depicts the completed battery. The carbonized material can be either directly used as an electrode or ground.

FIG. 6A is a photograph of growing *N. crassa* fungus. FIG. 6B is a SEM image of a hyphal matt before carbonization. FIG. 6C is a picture illustrating the biomass thermal conversion process wherein grown fungal material on the left is heated to produce the carbonized material on the right. FIG. 6D is a SEM image of carbonized hyphal matt. FIG. 6E is a SEM image of biocarbon tubes after carbonization. FIG. 6F is a FETEM image of cobalt nanoparticles imbedded in carbonized biocarbon tubes.

FIG. 8A reports nitrate consumption (diagonal) of *N. crassa* after 2-day mycelial growth using 20 mM (NO-20; right) and 40 mM $NaNO_3$ (NO-40; left) and subsequent C/N ratio (vertical). FIG. 8B reports comparison of the C/N and biomass production (horizontal) using 20 mM $NH_4NO_3$ (NH-20; right), 40 mM $NaNO_3$ (NO-40; center), and 10 mM $Co(NO_3)_2$ (FCCE; green).

DETAILED DESCRIPTION OF THE INVENTION

Figure 1A:
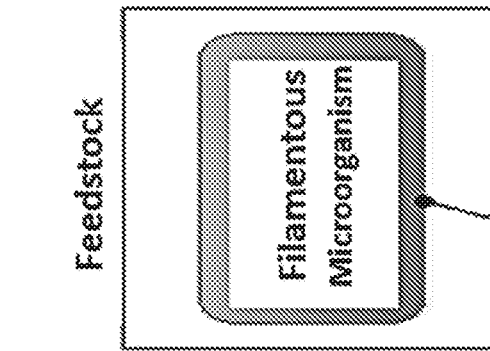
FIGS. 1A-1C are an illustrative flowchart of a method of converting filamentous microorganisms into carbonaceous materials.

The invention relates in one aspect to the unexpected discovery that filamentous fungal mats incubated in growth media comprising certain inorganic and/or organic compounds incorporate those compounds, and that pyrolysis of the doped fungal mats can produce carbonaceous materials with desirable properties. In certain embodiments, these carbonaceous materials can be used as electrodes in solid state batteries. In other embodiments, these carbonaceous materials can be used as electrodes in solid state batteries and/or lithium-ion batteries.

In one aspect, the invention provides carbonaceous materials which are suitable for use as electrodes, catalytic surfaces and adsorbents. In another aspect, the invention provides methods of producing carbonaceous electrode materials from filamentous fungus. In yet another aspect, the invention provides battery devices incorporating the carbonaceous electrode materials.

Definitions

As used herein, each of the following terms has the meaning associated with it in this section.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described. Generally, the nomenclature used herein and the laboratory procedures in mycology, materials engineering and materials chemistry are those well-known and commonly employed in the art.

As used herein, the articles "a" and "an" refer to one or to more than one (i.e., to at least one) of the grammatical object of the article. By way of example, "an element" means one element or more than one element.

As used herein, the term "about" is understood by persons of ordinary skill in the art and varies to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "biomass" refers to organic matter derived from living or previously living organisms. Biomass can include plant or plant-based materials, as well as fungi or fungus-based materials, bacteria or bacteria-based materials, algae or algae-based materials, plankton and plankton-based materials, and less commonly animal and animal-based materials. Biomass can be derived from commonly disposed of waste materials.

As used herein, the term "carbonaceous" refers to a material that relates to, contains or is composed at least partially of carbon. In certain embodiments, carbonaceous materials referred to herein are those that comprise more carbon (w/w) than any other individual element.

As used herein, the terms "carbonize" and "carbonization" refer to a process by which organic substances are converted through thermal conversion of biomass. Thermal conversion can include pyrolysis, gasification, hydrothermal, and microwave.

As used herein, the term "fungal mats" or "mycelial mats" refers to the mycelium of the vegetative part of a fungus, comprising the branching, thread-like hyphae.

As used herein, the term "fungi" or "fungus" is any member of the group of eukaryotic organisms that includes unicellular microorganisms such as yeasts and molds, as well as multicellular fungi that produce fruiting forms known as mushrooms.

As used herein, the term "lyophilize" refers to a process of "freeze-drying" a material by lowering both the temperature and pressure on a material in order to cause the sublimation of water in the material.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following abbreviations are used herein: BED, Brunauer-Emmett-Teller; C/D, charge/discharge; CNT, carbon nanotubes; EIS, Electrochemical impedance spectra; FE-TEM (or FETEM), Field emission scanning electron microscopy; *N. crassa, Neurospora crassa*; PVDF, polyvinylidene fluoride; SEM, scanning electron microscopy; TEM, transmission electron microscopy; XRD, X-ray diffraction; XPS, X-ray photoelectron spectroscopy Compositions The invention includes carbonaceous materials comprising a graphitic, partially graphitic, or amorphous carbon matrix derived from a filamentous organism, such as but not limited to a fungus. In certain embodiments, the filamentous organism is converted into a carbonaceous material by heating the organism to a temperature sufficient to carbonize the organisms. In certain embodiments, the carbonization process occurs under a controlled atmosphere.

In certain embodiments, the carbonaceous material is a free-standing material, which is continuous in nature and does not comprise a binder. In other embodiments, the carbonaceous material is porous throughout the entirety of the material. In yet other embodiments, the material is graphitic. In yet other embodiments, the material is partially graphitic.

In certain embodiments, the filamentous organisms are one or more selected from the group consisting of filamentous algae, filamentous fungi and filamentous bacteria. In other embodiments, the filamentous fungus is wild type or genetically modified *Neurospora crassa*.

In certain embodiments, the material comprises a carbonaceous materials doped with impurities that modulate the chemical, physical and/or electrochemical properties of the carbonaceous material. In other embodiments, the material comprises carbon and hydrogen, and further comprises one or more non-carbon atoms. In yet other embodiments, the non-carbon atoms can be selected from the group consisting of silicon, nitrogen, oxygen, sulfur, cobalt, sodium, magnesium, nickel, zinc, manganese and iron. In other embodiments, the doped non-carbon atoms are uniformly distributed throughout the material. In yet other embodiments, the doped non-carbon atoms form clusters or (nano)particles within the carbon matrix. In yet other embodiments, the doped non-carbon atoms form particles. In yet other embodiments, these particles can be metal particles, metal nanoparticles or metal-oxide nanoparticles. In yet other embodiments, the material comprises $Co_2O_3$ nanoparticles. In yet other embodiments, the material comprises one or more plastics.

In certain embodiments, the doped elements are incorporated into the filamentous organisms by adding one or more inorganic and/or organic compounds to the culture medium in which the organisms are being grown. In other embodiments, the compounds are added to the culture medium in concentrations ranging from about 0.001 mM to about 10 M, 0.01 mM to about 10 M, 0.1 mM to about 10 M, 0.001 mM to about 1 M, 0.01 mM to about 1 M, 10 mM to about 40 mM, or 0.1 mM to about 1 M. In yet other embodiments, the one or more compounds comprise non-carbon elements selected from the group consisting of transition metals, lanthanides, actinides, alkali metals, alkaline earth metals, metalloids, and post-transition metals. In yet other embodiments, the one or more inorganic compounds are selected from cobalt, sodium, magnesium, nickel, zinc, manganese, and iron salts, particles and oxides and silicon particles. In yet other embodiments, one or more inorganic compounds are selected from the group consisting of silicon nanoparticles, cobalt nitrate, sodium nitrate, ammonium nitrate and magnesium sulfate. In yet other embodiments, plastics are added to the culture medium.

In certain embodiments, the carbon matrix has an average pore size ranging from about 0.1 nm to about 10 mm. In other embodiments, the carbon matrix has an average pore volume of about 1 Å to about 2,000 Å. In other embodiments, the carbon matrix has an average pore volume of about 1,100 Å. In certain embodiments, the carbon matrix has a hierarchal pore structure. In certain embodiments, the graphitic carbon matrix retains, and/or significantly retains, the 3D pore integrity of the pre-carbonization biological matter.

In certain embodiments, the carbonaceous material is produced by heating the filamentous organisms to a maximum temperature of about 100° C. to about 2,500° C. In other embodiments, the carbonaceous material is produced by heating the filamentous organisms to a maximum temperature of about 800° C. to about 1,000° C. In other embodiments, the filamentous organisms are heated from room temperature to the maximum temperature. In yet other embodiments, the filamentous organisms are heated from room temperature to the maximum temperature at a rate of about 20° C./min. In other embodiments, the filamentous organisms are heated at the maximum temperature for about 2 hours. In certain embodiments, the organisms are heated in the presence of a gas comprising nitrogen, oxygen, air, argon, hydrogen sulfide, ammonia and/or an inert gas. In other embodiments, the gas comprises, consists essentially of, and/or consists of nitrogen gas. In yet other embodiments, the gas flows over the filamentous organisms at a rate between about 10 mL/min and 1000 mL/min. In certain embodiments, the carbonaceous material is subjected to an activation step prior to or after heating. In other embodiments, the activation can be a chemical or physical treatment.

In certain embodiments, the carbonaceous materials are substantially cylindrically shaped. In other embodiments, the carbonaceous materials of the invention are suitable for use as a battery electrode. In yet other embodiments, the carbonaceous materials of the invention are suitable for use as an electrode for electrochemical catalysis. In yet other embodiments, the carbonaceous materials are suitable for use as adsorbents.

Methods

The invention further provides methods of producing the carbonaceous materials of the invention, such can be for example electrodes. In certain embodiments, the carbonaceous material comprising a graphitic or partially carbon matrix is produced by incubating a sample of a filamentous organism in a culture medium comprising one or more inorganic and/or organic compounds for a period of time. In certain embodiments, the incubation of the filamentous organism occurs under light. In other embodiments, the incubation of the filamentous organism occurs in the dark. In other embodiments, the method further comprises harvesting the filamentous organism and washing it with a solvent, such as deionized water, one or more times. In yet other embodiments, the method further comprises drying the washed filamentous organism to form a dried organic material. In yet other embodiments, the method further comprises, optionally, grinding the dried organic material into a powder and mixing the powder with a polymeric binding material. In yet other embodiments, the method further comprises flash freezing and lyophilizing the washed filamentous fungus to form a lyophilized fungal material. In yet other embodiments, the method further comprises shaping or pressing the dried organic material into a desired shape. In yet other embodiments, the method further comprises contacting a conductive wire with the lyophilized fungal material. In yet other embodiments, the method further comprises carbonizing the lyophilized organic material by heating it in contact with a gas.

In certain embodiments, the filamentous organism is one or more selected from the group consisting of a filamentous algae, filamentous bacterium and filamentous fungus. In other embodiments, the filamentous fungus is wild type or genetically modified *Neurospora crassa*.

In certain embodiments, the filamentous organism is incubated for about 1 to about 5 days. In yet other embodiments, the culture medium is 1× Vogel's culture medium, wherein 1× Vogel's medium comprises 2% Vogel's salts, 0.01% trace elements solution, 0.005% biotin and 2.0% glucose. In yet other embodiments, the filamentous organism is incubated at about 25-35° C. In yet other embodiments, the filamentous organism is incubated for about 1 to about 5 days under constant light.

In certain embodiments, inorganic compounds are added to the culture medium in concentrations ranging from about 10 mM to about 40 mM. In yet other embodiments, one or more inorganic compounds are selected from the group consisting of metal salts and any other inorganic chemicals, such as silicon particles, cobalt salts, sodium salts, magnesium salts, nickel salts, zinc salts, manganese salts, and iron salts. In yet other embodiments, one or more inorganic compounds are selected from the group consisting of silicon nanoparticles, cobalt nitrate, sodium nitrate, ammonium nitrate and magnesium sulfate. In yet other embodiments, magnesium sulfate is added to the culture medium alongside cobalt nitrate. In yet other embodiments, magnesium sulfate counteracts any possible toxic effects of cobalt nitrate on the organism.

In certain embodiments, after harvesting, the filamentous organism is washed with a solvent. In other embodiments, the filamentous organism is washed with deionized water. In yet other embodiments, the filamentous organism is washed one or more times to remove any impurities. In yet other embodiments, the filamentous organism is washed at least two times. In yet other embodiments, the washing is done by centrifuging the filamentous organism with deionized water. In yet other embodiments, the filamentous organism is centrifuged before the supernatant is removed. In yet other embodiments, the filamentous organism is centrifuged at about 12,000 RPM for about 10 minutes before the supernatant is removed.

In certain embodiments, the filamentous organism is dried by flash freezing. In other embodiments, this is done by contacting the organism with liquid nitrogen. In other embodiments, the flash frozen material is lyophilized overnight to produce a dehydrated organic material. In yet other embodiments, the lyophilized material is pressed into a desired shape by pressing it into a vessel. In yet other embodiments, the lyophilized material is ground into a powder. In yet other embodiments, a binding material is added to the powdered lyophilized material. In yet other embodiments, the lyophilized material is pressed around a conducting wire or a conducting wire is threaded into the lyophilized material. In yet other embodiments, the filamentous organism is dried by heating the material at a low heat that is not hot enough to cause carbonization.

In certain embodiments, the dried organic material is carbonized by heating the material under a gaseous atmosphere. In other embodiments, the carbonaceous material is produced by heating the filamentous organism to a maximum temperature of about 800° C. to about 2,000° C., or about 800° C. to about 1,000° C. In yet other embodiments, the filamentous organisms are heated from room temperature to the maximum temperature gradually. In yet other embodiments, the filamentous organisms are heated from room temperature to the maximum temperature at a rate of about 20° C./min. In yet other embodiments, the filamentous organism is heated at the maximum temperature for about 2 hours. In yet other embodiments, the gaseous atmosphere comprises nitrogen, oxygen, air, ammonia, hydrogen sulfide, steam or an inert gas. In other embodiments, the gaseous atmosphere comprises pure nitrogen gas. In yet other embodiments, the gas is made to flow over the filamentous organism at a rate between about 10 mL/min and 100 mL/min.

In certain embodiments, the methods of the invention allow for the synthesis of a range of carbonaceous materials with varying properties by modifying one or more variables selected from: species or genetic makeup of the organism, growth medium, inorganic and/or organic materials added to the growth medium, concentration of the inorganic and/or organic materials added to the growth medium, pH of the growth medium, growth period and conditions including temperature, mixing rate and flow rate of the growth medium, temperature, light and ramp rate of the carbonization process, and content and flow rate of the controlled atmosphere during the carbonization process.

The invention further includes a method of removing pollutants from wastewater sources while simultaneously producing filamentous organic biomass that can be converted into carbonaceous materials. In certain embodiments, a filamentous organism is grown in a wastewater medium, absorbing and integrating organic and/or inorganic matter from the wastewater, removing the matter from the wastewater source and thus purifying it. In other embodiments, the organic biomass is then used as-is or converted into carbonaceous material.

Devices

The invention further includes battery devices comprising a carbonaceous electrode material of the invention. In certain embodiments, the battery devices comprise a carbonaceous electrode of the invention and a solid state electrolyte. In other embodiments, the electrolyte comprises 7.5Li$_2$S-22.5P$_2$S$_5$ glass (a77.5). In yet other embodiments, the battery devices comprise a carbonaceous electrode of the invention and a lithium ion electrolyte. In yet other embodiments, the lithium ion electrolyte comprises LiPF$_6$. In yet other embodiments, the battery device comprises a carbonaceous electrode of the invention, which has been doped with a transition metal or silicon. In yet other embodiments, the battery device comprises a carbonaceous electrode of the invention, which has been doped with cobalt.

In certain embodiments, the doped carbonaceous electrode of the battery device has a discharge capacity greater than that of standard graphite (370 mA·h/g). In certain embodiments, the doped carbonaceous electrode of the invention is suitable for use in high capacity batteries.

The invention further includes catalytic reactor devices that comprise a carbonaceous material of the invention. In certain embodiments, the catalytic reactor device comprises one or more carbonaceous materials of the invention doped with one or more catalytically active transition metals. In certain embodiments, a voltage can be applied to the one or more carbonaceous materials in order to drive a catalytic oxidation reaction or a catalytic reduction reaction.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods

Cell Maintenance and Isolation of Conidia

*Neurospora crassa* (*N. crassa*) wild-type strain (FGSC #262) was purchased from the fungal genetic stock center. The cells used for inoculations were stored on agar slants composed of 2% Vogel's 50× salts, 0.01% trace elements solution, 0.005% biotin, 1.5% sucrose, and 1.5% agar at −20° C. Growth experiments were started from cells removed from frozen agar slants onto new agar slants incubated at 30° C. for 2-3 days in complete darkness. Conidia were isolated from slants using standard methods and inoculated into 100 mL of fresh Vogel's medium (2% Vogel's 50× salts, 0.01% trace elements solution, 0.005% biotin, and 1.0% glucose) for batch submerged culture experiments. Conidial suspensions (1 mL in Vogel's medium) between optical densities of −0.7 were added to each culture.

Batch Growth Experiments

Growth experiments were conducted in 50 mL of fresh culture composed of 2% modified Vogel's 50× salts, 0.01% trace elements solution, 0.005% biotin, and 2% glucose. Batch cultures were incubated at 30° C. for 3-5 days (120 rpm) under constant light. The modification to the Vogel's 50× salts included defined concentrations (10 mM, 20 mM, and 40 mM) of sodium nitrate (NaNO$_3$) or cobalt metal salts in comparable concentrations of NO$_3^-$ anions. *N. crassa* growth experiments with Co(NO$_3$)$_2$ were performed with a 1:1 molar ratio of Mg$^{2+}$ in the form of MgSO$_4$. Experiments designed for evaluating the amount of cobalt adsorbed by heat-killed biomass were performed using 48 hr submerged autoclaved (15 min, 121° C.) cultures soaked in the same molar concentration of $Co(NO_3)_2$ as growth experiments for 24 hrs. Fungal mats from all experiments were washed (2×) with DI water, centrifuged at 12,000 RPM for 10 min, and the supernatant was removed. The harvested fungal cells were then flash frozen with liquid $N_2$ and lyophilized overnight.

Thermal Conversion of Fungal Biomass into Graphitic Electrode

The lyophilized biomass (100 mg) was first pressed into an aluminum oxide crucible (900 uL; 10 mm circumference×10 mm deep) and a 10 cm annealed titanium wire (Goodfellow Cambridge Limited; 0.25 mm diameter) was threaded into the biomass. The lyophilized fungal biomass was thermally converted in a thermogravimetric analyzer (TGA) (Mettler-Toledo (TGA-DSC1); Star$^e$ software package). Thermal conversion proceeded at a heating rate of 20° C. $min^{-1}$ with a highest heat temperature of 800° C. under UHP $N_2$. The protective gas (UHP $N_2$) flow rate was 100 mL $min^{-1}$ and reactive gas (UHP $N_2$) flow rate was 10 mL $min^{-1}$. The wired self-standing carbonized electrode was used "as-is" with no post-treatment for electrochemical measurements.

Physical and Elemental Characterization

The morphology and structure of the fungal cells and fungal derived electrode material were investigated using scanning electron microscopy (SEM; Jeol JSM-6480LV, 30 kV). Elemental analysis was determined by Robertson Microlit Laboratories, Inc (Ledgewood, N.J.). Microstructure for all fungal derived electrode materials were characterized by powder X-ray diffraction spectroscopy (XRD) using a Rigaku 18-Kw X-ray generator and high resolution powder diffractometer with Cu-Ka radiation derived from a rotating anode X-ray source operated at 50 kV and 200 mA. Brunauer-Emmett-Teller (BET) method using a five-point $N_2$ gas adsorption technique (ASAP 2020; Micromeritics, Norcross, Ga.) was used to measure the specific surface area and pore size distribution of the fungal derived electrode materials. X-ray photoelectron spectroscopy (XPS) was performed using a SPECS Phobios 150MCD with Mg K source.

High Performance Liquid Chromatography Conditions

Samples were collected from each batch culture at 24 hr intervals for 72 hrs. At each time point 1.0 mL of culture medium was collected from each growth condition and analyzed for glucose and nitrate concentration using liquid chromatography. Glucose separations were performed using a Varian Prostar HPLC with diode array and refractive index detectors.

Glucose analysis was performed with a Hi-plex $H^+$ column (300×7.7 mm) held at 65° C. with a 5 mM $H_2SO_4$ mobile phase at 0.6 mL $min^{-1}$ flow rate. Ion chromatography was performed using a Dionex ICS-3000 using a Dionex IonPac™ AS9-HC (4×250 mm). The flow rate was 1.0 mL $min^{-1}$ using a 9 mM sodium carbonate mobile phase. The concentrations of glucose and nitrate were determined independently using calibrated external standards.

Electrochemical Measurements

Stationary electrode cyclic voltammetry was performed in a 150-mL glass RDE cell (Pine Instruments) with $N_2$-saturated 0.1 M KOH for each free standing fungal derived electrode material. An Ag/AgCl reference electrode (Pine Instruments) and frit-isolated Au-foil counter electrode completed the electrochemical circuit. Electrochemical potentials and potential waveforms were applied to the working electrode for the electroanalytical experiments using a bipotentiostat (Pine Instruments AFCBP1) under computer control (Aftermath™ software, Pine Instruments). Electrochemical impedance spectra (EIS) was conducted by a potentiostat (PC4/3000, Gamry Instruments, NJ, USA) to determine total resistance using the fungal derived electrode material as the working electrode, and the titanium wire as counter electrode and Ag/AgCl reference electrode over a frequency range of 104 Hz to 0.01 Hz. The EIS analysis was carried out at room temperature in 0.1 M KOH electrolyte.

Figure 1B:
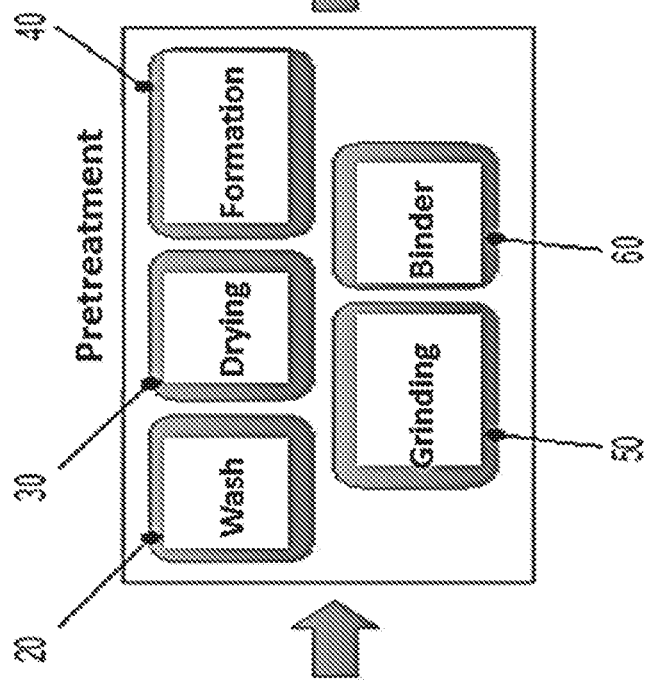
Figure 1C:
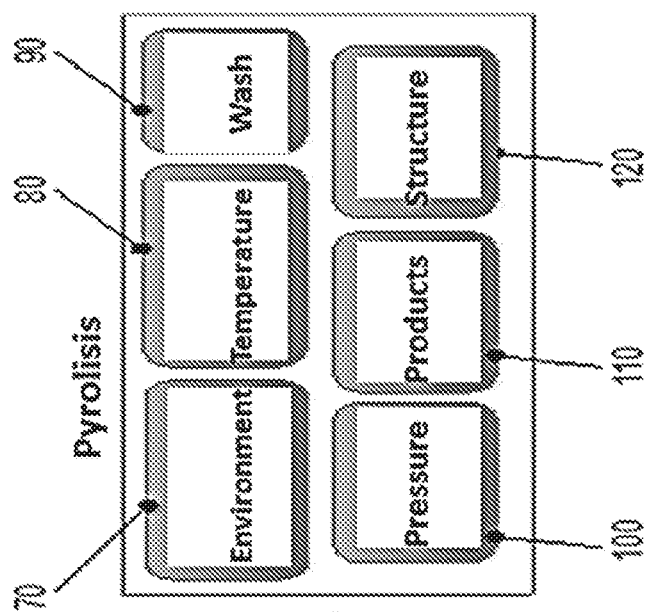
Figure 3A:
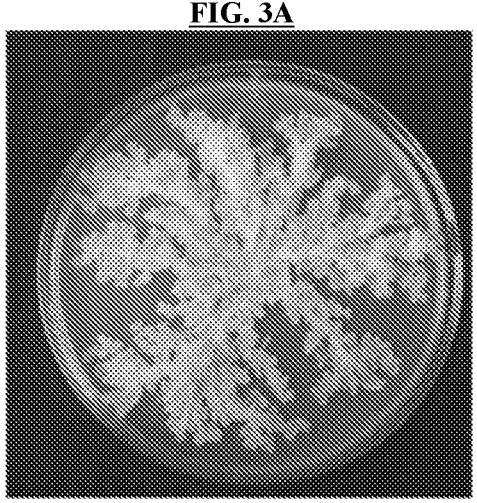
FIGS. 3A-3B comprise photographs depicting different fungal morphologies controlled by the alteration of the fungal organism's DNA.
Figure 3B:
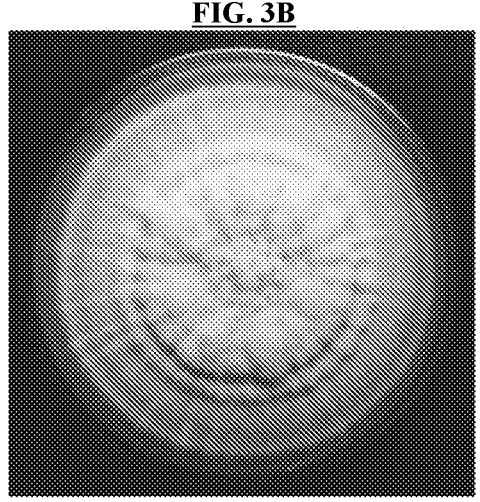

Example 1: General Procedure for the Production of Carbonaceous Materials from Filamentous Microorganisms The present invention includes methods for producing carbonaceous materials from filamentous microorganisms, including fungi. FIGS. 1A-1C is a flow chart illustrating the general procedures by which this is accomplished. First, the filamentous microorganisms are obtained through harvesting, collection or purchase (10). The microorganism is then washed (20); the washing media can include water solutions and organic solutions, both acidic and basic. Next, the microorganism is, optionally, dried (30). This can be accomplished by air drying or oven drying in a controlled environment at a temperature below 200° C. Alternatively, the microorganism can be lyophilized in a commercial chamber. The microorganism can, optionally, then be formed into a specific size or shape using a compressive load either during or after drying (40). The microorganism based material can, optionally, be ground to reduce particle size, depending on the intended use for the material (50). The material can, optionally, be mixed with a binder, also depending on the intended use for the material (60). Process 20-60 can be alternatively carried out in any reasonable order.

After pretreating the microorganism based material through the steps above, the material is then pyrolyzed in order to convert the material from biomass to carbonaceous materials. The material can be heated to a desired temperature at which carbonization takes place (70). The material carbonization takes place in an atmospherically controlled environment in which the desired amount of oxygen, nitrogen, argon, ammonia, air, and so forth, present is controlled. The carbonization process can take place with a single step heat treatment or a two stage heat treatment (80). A two stage heat treatment is one wherein the microorganism material is heated to a low temperature (pre-carbonization) and held for a given amount of time. The temperature can then be increased to a temperature greater than the first temperature and held for a second given amount of time. The heating rate (90) and the external pressure (100) can be controlled during the carbonization process. Any gaseous byproducts produced by the pyrolysis process can be collected and used as fuel or recycled into the feedstock for the carbonization reaction (110). Carbonized material may or may not contain graphitic domains once pyrolysis is complete (120).

Example 2: Growth and Assimilation of Silicon Nanoparticles with Actively Growing *N. crassa*

Figure 6A:
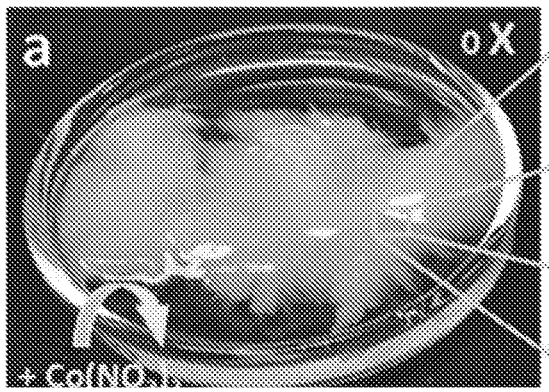
FIGS. 6A-6F comprise an array of photographs depicting fungal material before and after thermal conversion.
Figure 6B:
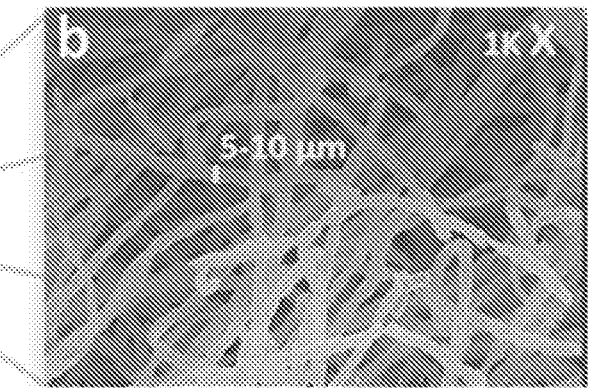
Figure 6C:
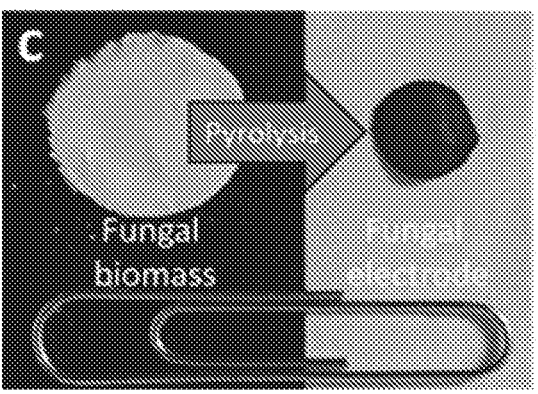
Figure 6D:
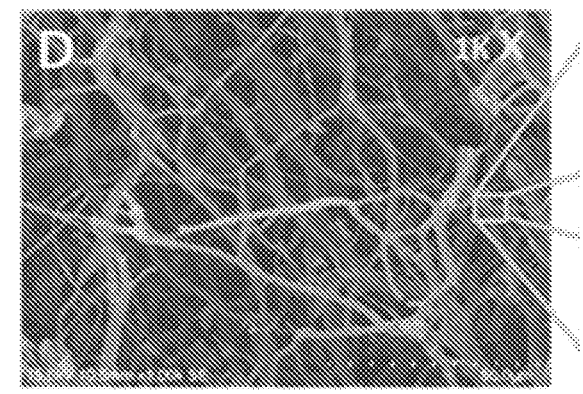
Figure 6E:
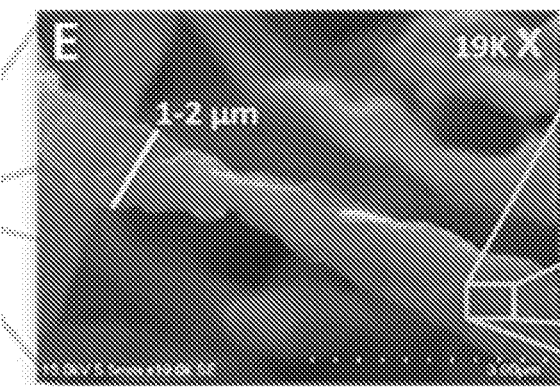
Figure 6F:
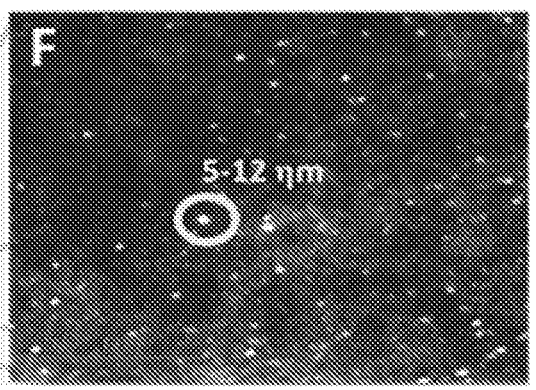
Figure 7A:
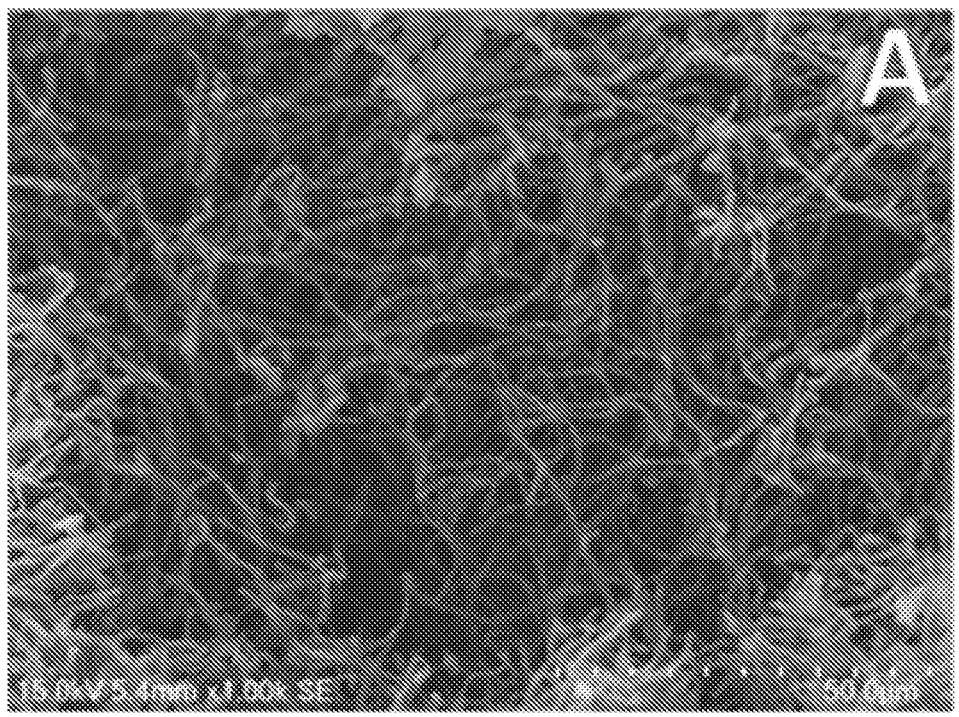
FIGS. 7A-7B comprise illustrative SEM images of fungal mats and hyphal structure of the NO-40 (FIG. 7A) and FCCE-S (FIG. 7B) materials.
Figure 7B:
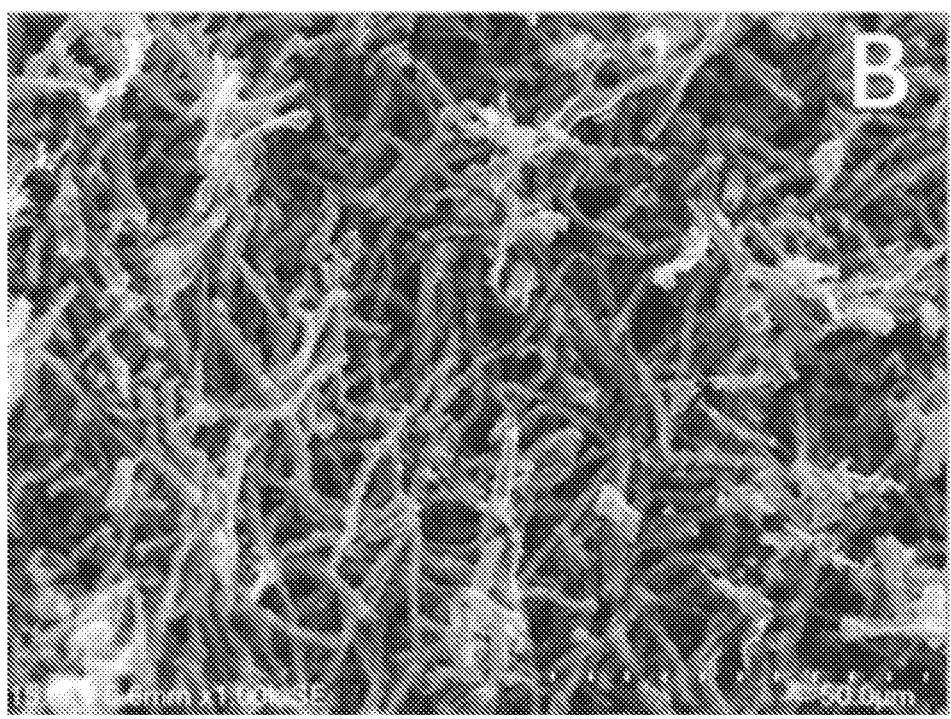

The selection of an effective and scalable biological template can consider the amount of biomass that can be generated, resilience of the organism to environmental stressors, and the growth potential (rate and structure) for the selected organism. *Neurospora crassa*, a well-characterized filamentous fungus, was selected as the living template for electrode fabrication based on its robustness in minimal nutrient media, high tolerance to an assortment of toxic metals, and is one of the fastest growing organism, with a linear growth rate of 3-6 mm h$^{-1}$ per hyphal tip. FIGS. 6A-6F show illustrative steps of the present method, from a filamentous fungal mats (FIG. 6A) to a 3D hyphal structures observed using the dried hyphal mats (FIG. 6B) to the carbon-based structures observed after thermal conversion (FIGS. 6D and 7A-7B).

Experiments were undertaken to utilize the adaptability of N. crassa to tune the chemical and structural properties of the resulting biomaterial by adding silicon nanoparticles to the growth medium of the fungus (FIGS. 2A-2C). It was observed that the fungus readily incorporated the silicon nanoparticles by encapsulating them. The process of Si encapsulation also includes the adsorption and chemical bonding of Si to various surface functional groups present on the fungal biomass.

Example 3: Growth and Assimilation of Co(NO$_3$)$_2$ with Actively Growing N. crassa Taking advantage of the natural adaptation of N. crassa, a methodology was developed to tune the chemical composition of the normal biomass toward electrochemical applications during growth. This includes control of the C/N ratio (determined from the elemental analyses in Table 1) of the biomass and the incorporation of cobalt ions in the biomass and subsequent graphitic material.

Figure 8A:
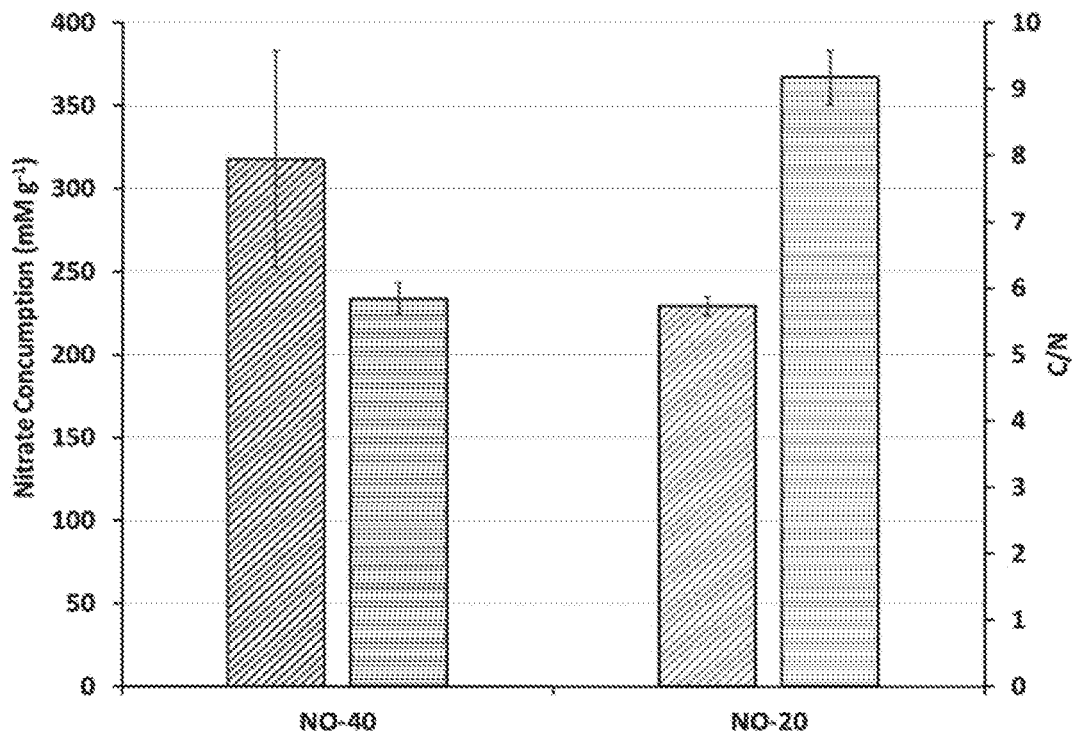
FIGS. 8A-8B comprise illustrative ion chromatography graphs reporting the results for nitrate consumption after 48 h of *N. crassa* growth from macroconidia in 111 mM glucose at 25° C.

The growth of N. crassa was accomplished by inoculating macroconidia isolated from sucrose slants in a modified Vogel's minimal medium without ammonium nitrate as the sole nitrogen source. Glucose was used as the sole carbon source at cells were cultured in light at 25° C. in liquid medium. Ammonium and nitrate are both viable nitrogen sources for N. crassa. The final C/N ratio for the bulk material using 20 mM NH$_4$NO$_3$ was 5.1±0.3, which was similar to the C/N ratio observed using 40 mM NaNO$_3$ as the sole nitrogen source (FIG. 8A and Table 1). All C/N ratios were calculated from the elemental analysis of the freeze-dried biomass and for the resulting graphitic material generated after pyrolysis.

The quantity of overall bulk dried biomass generated over 48 hrs was 92±0.2 mg and 100±0.5 for 40 mM NaNO$_3$ and 20 mM NH$_4$NO$_3$ respectively. In order to limit the amount of nitrate available during growth, a concentration of 20 mM NaNO$_3$ was used based on 19±1.5 mM of nitrate consumed during the 40 mM NaNO$_3$ experiment by anion chromatography. Under nitrate limited conditions the C/N ratio could be decreased by 26% using 40 mM NaNO$_3$. The C/N ratio could be increased using 20 mM NaNO$_3$ (FIG. 8A) because the rate of biomass formation was unaffected by nitrate limitations. These results confirm that, by limiting the sodium nitrate concentration the C/N ratio of the final material can be controlled, while not impeding the total amount of biomass ultimately produced.

Figure 8B:
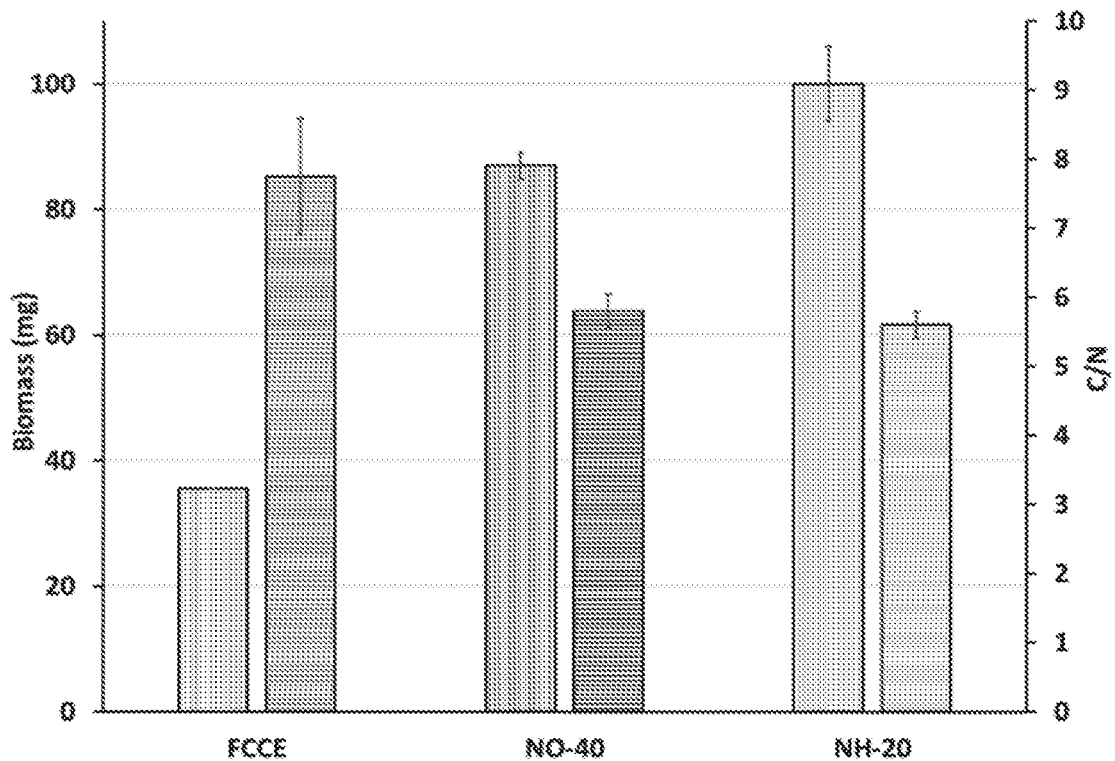

In an effort to incorporate Co(II) into the biomass directly during the growth of the organism, and ultimately into the carbon matrix of the electrode, N. crassa was cultivated in the presence of 10 mM Co(NO$_3$)$_2$ without any additional nitrogen source. All growth experiments that did not use equal molar concentrations of Mg$^{2+}$ to Co(II) did not result in significant growth of the organism. Slightly lower biomass production but similar C/N ratio (10±0.5) were observed from growth experiments that used Co(NO$_3$)$_2$ compared to only 40 mM NaNO$_3$ (FIG. 8B). These results are consistent with the presence of nitrate ions (by ion chromatography) when the cells were harvested leading to C/N ratios between 10-11 at the end of the growth period and confirms that Co(NO$_3$)$_2$ can be the sole source of nitrogen. The weight percentage of cobalt in the graphitic material generated when N. crassa was cultured with 10 mM Co(NO$_3$)$_2$ was 2.3%, which was significantly higher than the amount of cobalt observed from heat-killed fungal mats that were used as general biosorbants and thermally converted (0.84%; Table 1).

TABLE 1

Elemental composition of biomass and anode material generated from N. crassa fungal mats cultured with 10 mM Co(NO$_3$)$_2$ (FCCE), heat killed fungal mats soaked with 10 mM Co(NO$_3$)$_2$ (FCCE-S), 40 mM NaNO$_3$ (NO-40), 20 mM NaNO$_3$ (NO-20), and 10 mM NaNO$_3$ (NO-10)

| | Biomass | | | | Anode material | | | | | BET |
|---|---|---|---|---|---|---|---|---|---|---|
| Sample | C % | H % | N % | Co % | C % | H % | N % | Co % | C/N | (m$^2$/g) |
| FCCE | 43 ± 2 | 6.3 ± 0.3 | 6.4 ± 0.3 | 0.38 ± 0.022 | 55 ± 2 | 0.83 ± 0.04 | 5.5 ± 0.3 | 2.3 ± 0.1 | 10 ± 0.5 | 5.9 ± 0.3 |
| FCCE-S | 40 ± 2 | 5.9 ± 0.3 | 6.2 ± 0.3 | 0.13 ± 0.01 | 76 ± 4 | 0.76 ± 0.04 | 6.9 ± 0.3 | 0.80 ± 0.04 | 11 ± 0.5 | 3.9 ± 0.2 |
| NO-40 | 39 ± 2 | 6.1 ± 0.3 | 6.4 ± 0.3 | — | 63 ± 3 | 1.9 ± 0.1 | 6.5 ± 0.3 | — | 9.7 ± 0.5 | 4.3 ± 0.2 |
| NO-20 | 46 ± 2 | 7.1 ± 0.4 | 4.9 ± 0.2 | — | 67 ± 3 | 1.4 ± 0.7 | 5.1 ± 0.3 | — | 13 ± 0.6 | 1.4 ± 0.1 |
| NO-10 | 45± | 5.4 ± 0.3 | 3.3 ± 0.2 | — | 67 ± 3 | 2.1 ± 0.1 | 4.5 ± 0.2 | — | 15 ± 0.8 | 1.7 ± 0.1 |

Example 4: Growth of N. crassa in Wastewater Media

Figure 4A:
FIGS. 4A-4C comprise photographs depicting cultivation of filamentous fungi for remediation, resource recovery and material synthesis in a variety of wastewater media.
Figure 4B:
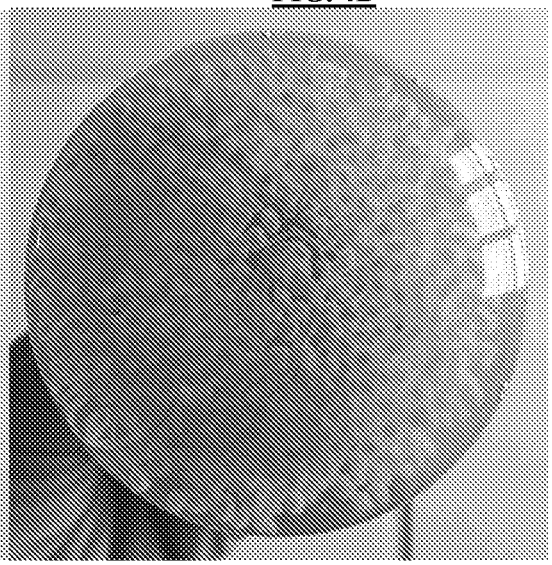
Figure 4C:
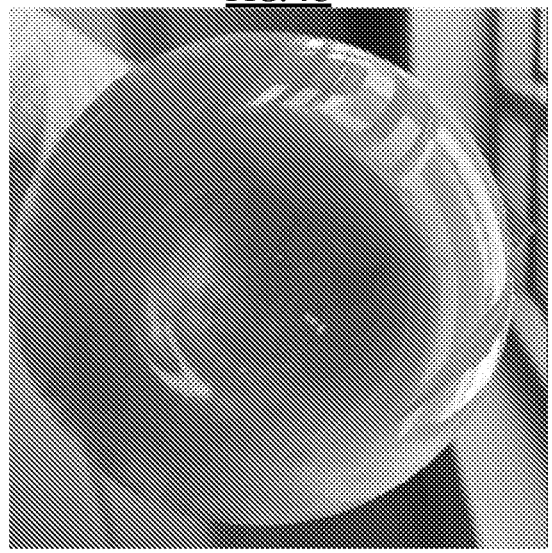

N. crassa's robustness allows for it to grow in environments that would normally be considered inhospitable for most microorganisms. This quality makes it an attractive carbon biomass source, because N. crassa can therefore be used to convert low utility waste materials into useful carbon based materials. Experiments were carried out to test the growth of N. crassa in a number of wastewater media, including municipal waste water (FIG. 4A), brewery wastewater (FIG. 4B) and iron sludge residue from a drinking water filtration plant (FIG. 4C). In all cases, the fungus grew and thrived. Additionally, the fungus grown in the iron sludge residue incorporated the iron oxide residue present in the growth medium into its fungal mat.

Example 5: Pyrolysis of Fungal Biomass and Retention of Biotemplated Structure

Figure 10:
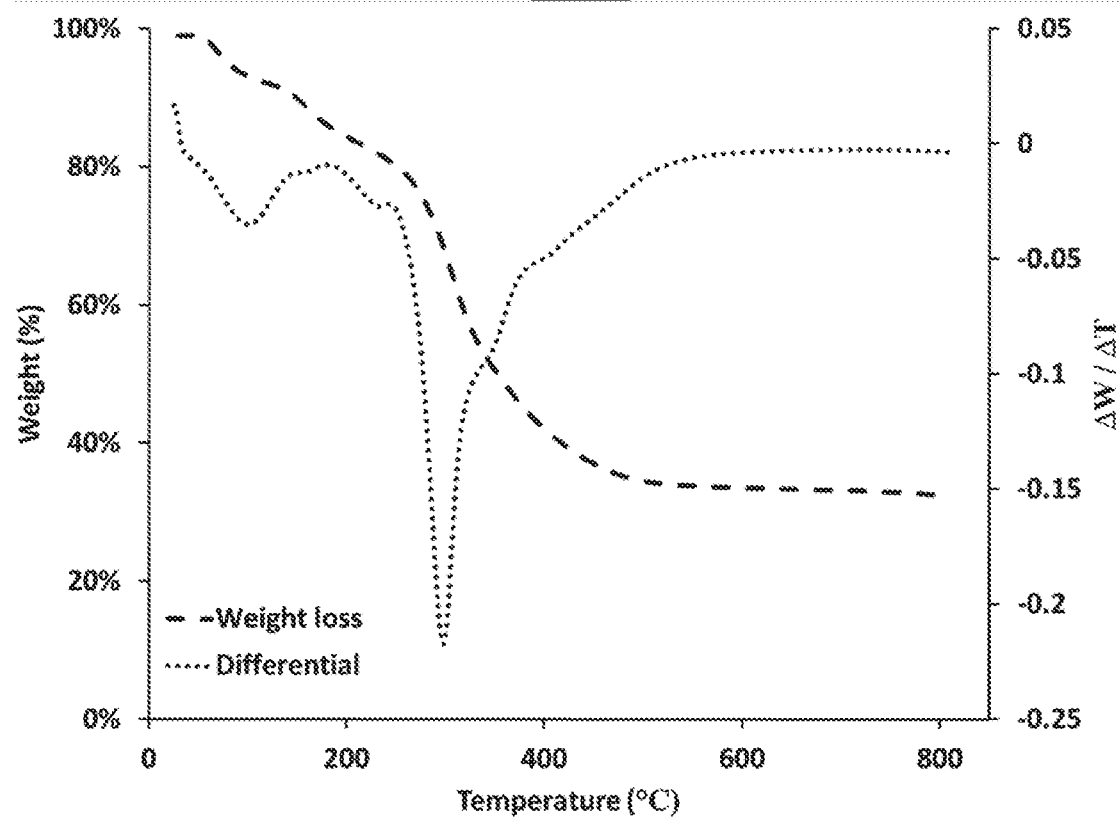
FIG. 10 comprises an illustrative graph tracking weight loss and differential data from pyrolysis of fungal mats of *N. crassa* at 20° C./min.

The conversion of fungal mats into graphitic materials was accomplished with pyrolysis under a nitrogen atmosphere. Pyrolysis converts the disordered chemical microstructure into a more ordered turbostratic structure. The thermal conversion of the biomass generated from growing N. crassa in 10 mM (NO-10), 20 mM (NO-20), and 40 mM (NO-40) sodium nitrate and cobalt nitrate (FCCE) or the absorption of cobalt by pre-grown and heat-killed fungal material soaked in cobalt nitrate (FCCE-S) were performed using identical heating cycles in a large oven thermogravimetric analyser. Pyrolysis of each material was performed using 80-100 mg of vacuum-dried biomass pressed into ceramic crucibles. Based on thermogravimetric data, it was observed that a major weight loss event occurs at around 300° C. with a total weight loss of 80% at the end of the experiment (FIG. 10).

Figure 11:
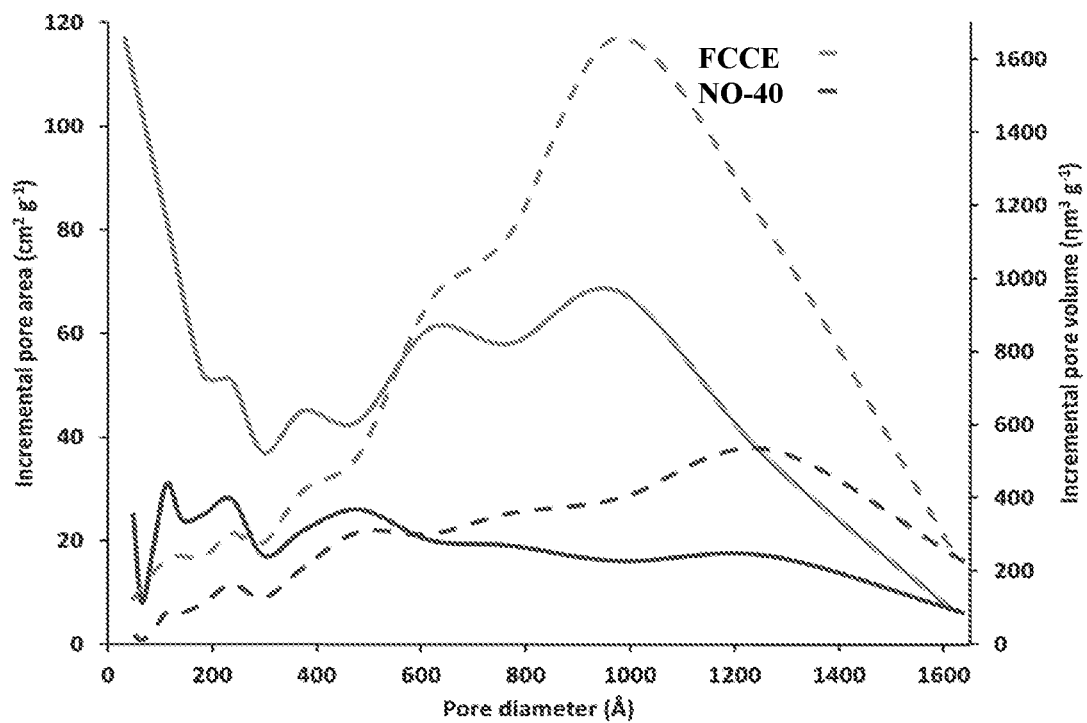
FIG. 11 comprises an illustrative graph of the incremental pore volume (dashed) and incremental pore area (solid) for FCCE and NO-40 electrode materials.
Figure 12:
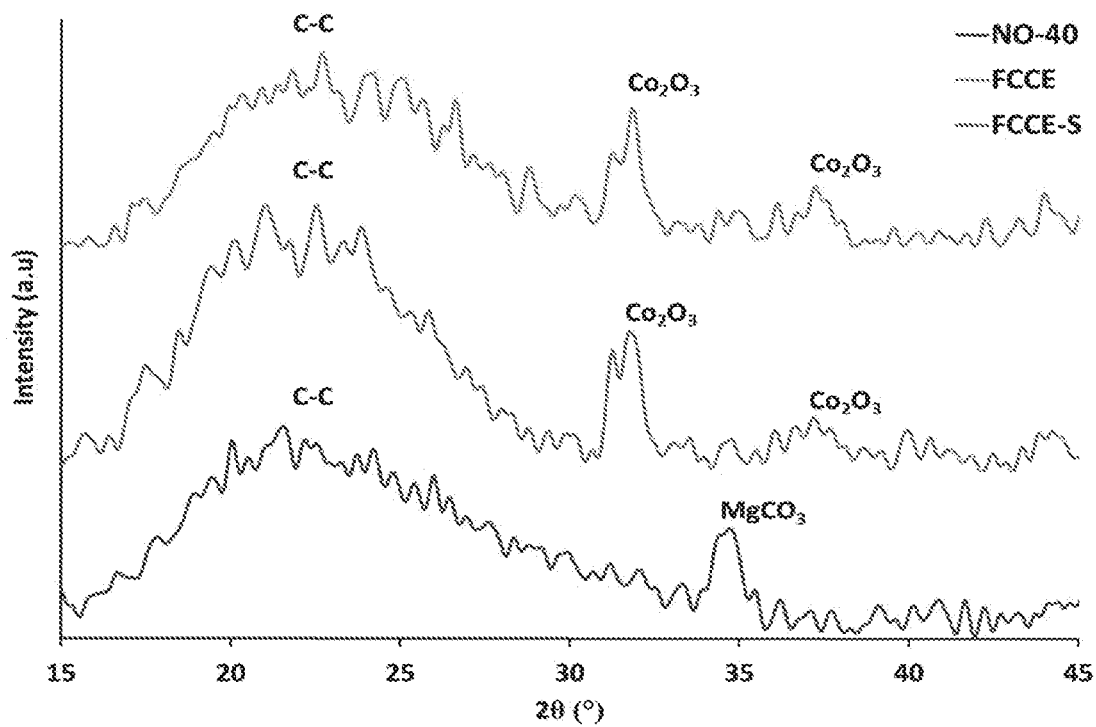
FIG. 12 illustrates non-limiting XRD spectra of FCCE (top), FCCE-S (middle) and NO-40 (bottom) illustrating dominant carbonate peaks.

The graphitic material that was isolated was a free-standing structure that maintains the 3D pore integrity of the parent material determined by SEM (FIGS. 6D and 7A-7B). The larger pore size (also observed by SEM) resulted in the low (1-5 $m^2$ $g^{-1}$) Brunauer-Emmett-Teller (BET) surface area calculated for each material (Table 1). The average pore volume for each material was around 1100 Å (FIG. 11). The biomass materials that were limited in nitrate during growth (NO-10 and NO-20) showed significantly lower surface areas than all other materials and this difference could not be attributed to changes in the 3D pore structure seen by SEM. Based on elemental analysis, the amount of cobalt associated with FCCE and FCCE-S graphite materials were 3× greater for the material generated from culturing *N. crassa* with 10 mM $Co(NO_3)_2$ instead of soaking the heat-killed material. There was no significant accumulation of magnesium in the material based on elemental analysis and powder x-ray diffraction (XRD) results (FIG. 12).

Figure 9:
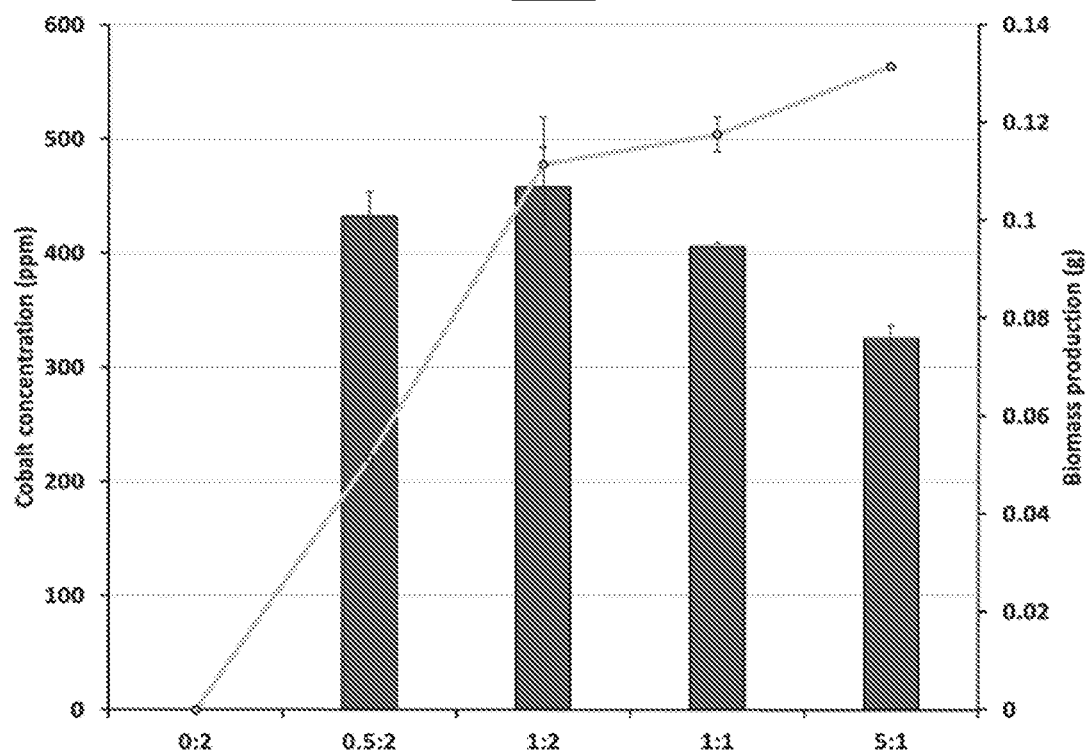
FIG. 9 comprises an illustrative graph of cobalt concentration (bars) and biomass production (line) of 48 hr *N. crassa* cultures grown in various molar concentrations of Co and Mg.

The XRD spectra shown in FIG. 9 confirms the graphitic nature of the material with the broad reflections between 15-35° indicating small domains of coherent stacking. The presence of $MgCO_3$ (observed at 34°) was observed with only the NO-40 material and was absent in the materials exposed to cobalt. The form of cobalt in both the FCCE and FCCE-S materials was tentatively confirmed to be $Co_2O_3$ by XRD and high resolution transmission electron microscopy (TEM). It was difficult to acquire enough signal from the cobalt nanoparticles to generate elemental maps of the hyphal surface because of the average 1 nm size of the $Co_2O_3$ nanoparticles observed by TEM (FIG. 6F). These cobalt nanoparticles were only observed in the carbonized hyphal structures grown with cobalt nitrate (FCCE) but not the soaked material (FCCE-S).

Figure 13A:
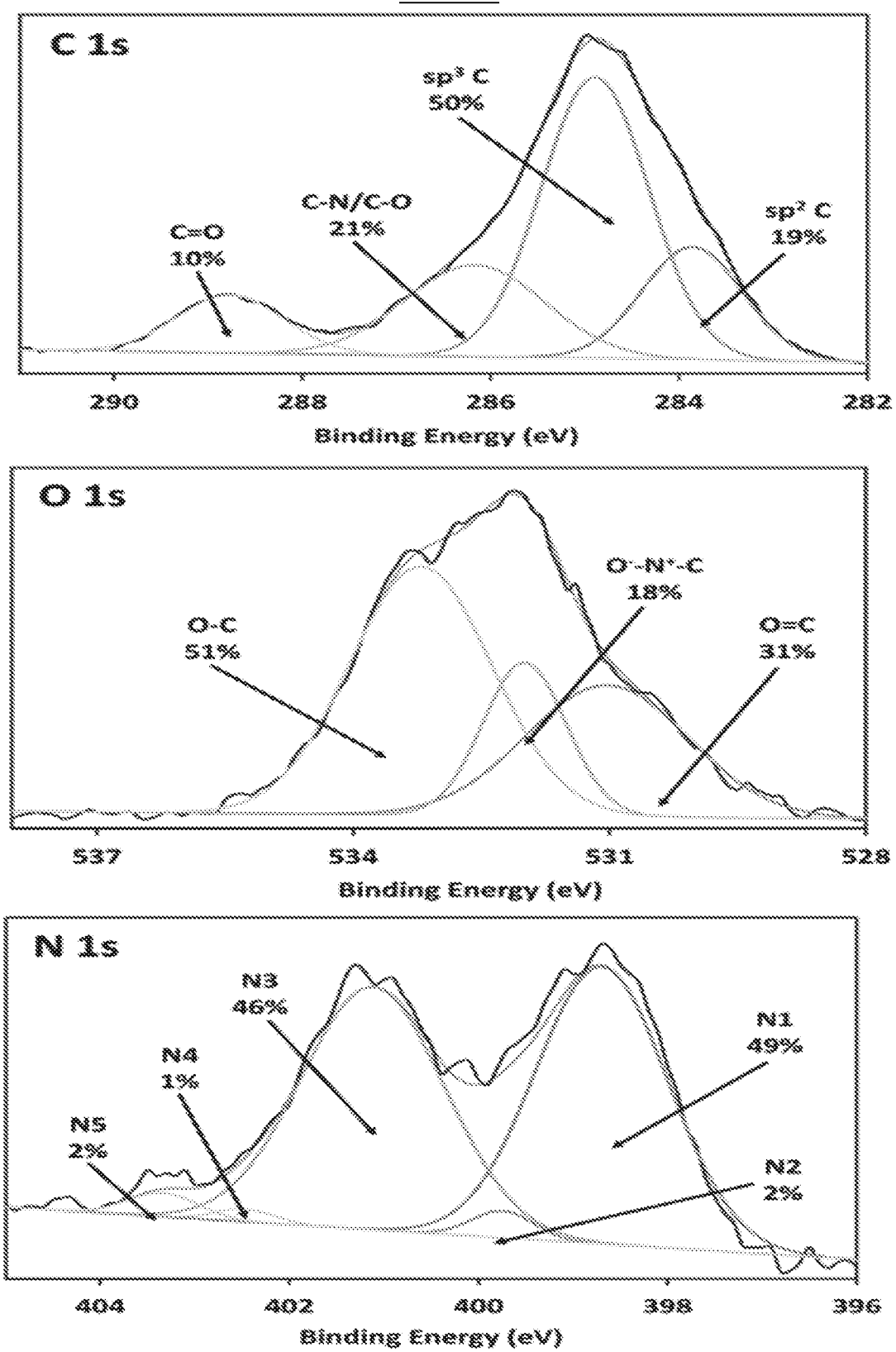
FIGS. 13A-13C illustrates non-limiting XPS spectra for FCCE (FIG. 13A), NO-40 (FIG. 13B) and FCCE-S (FIG. 13C).
Figure 13B:
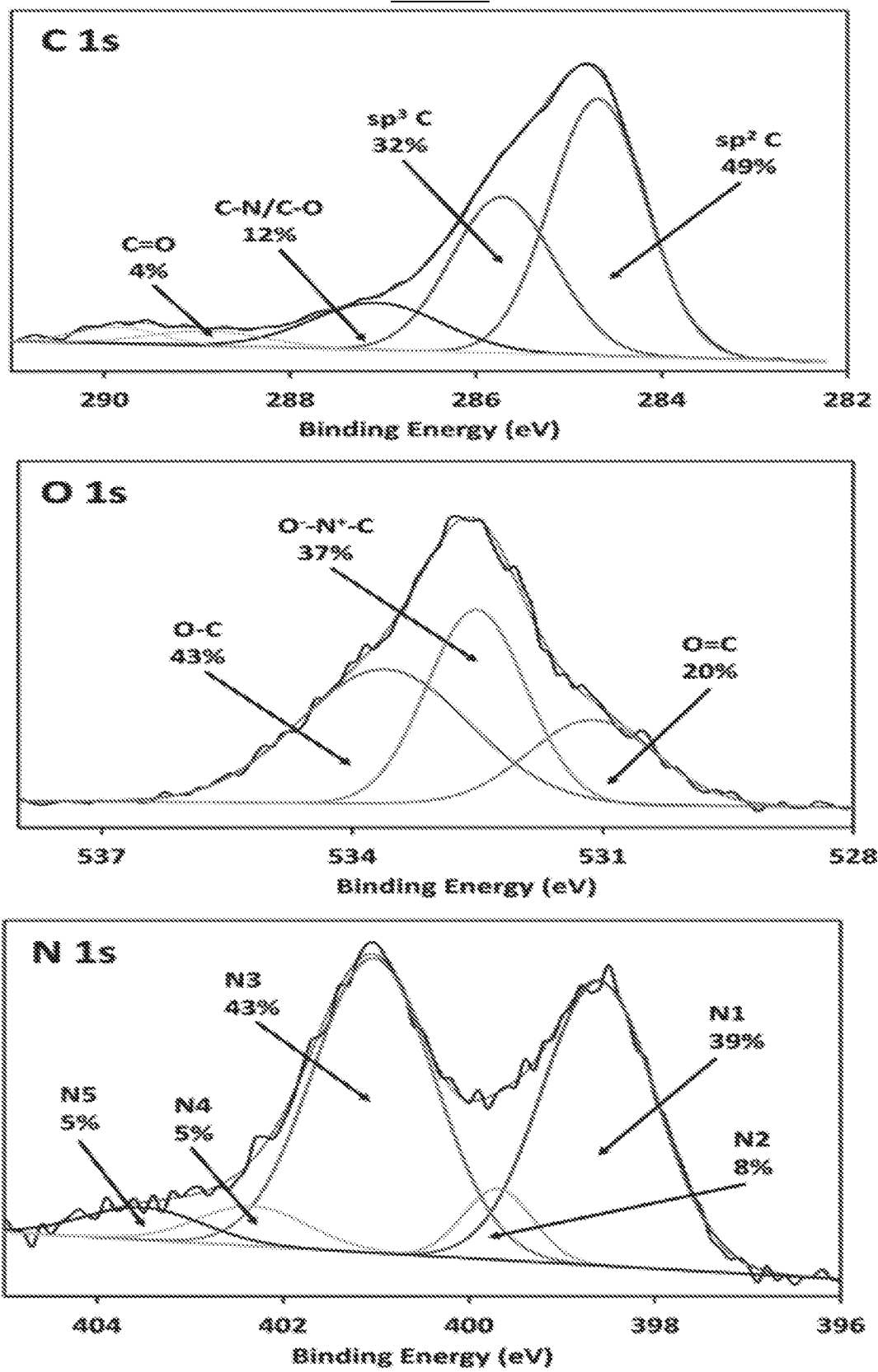
Figure 13C:
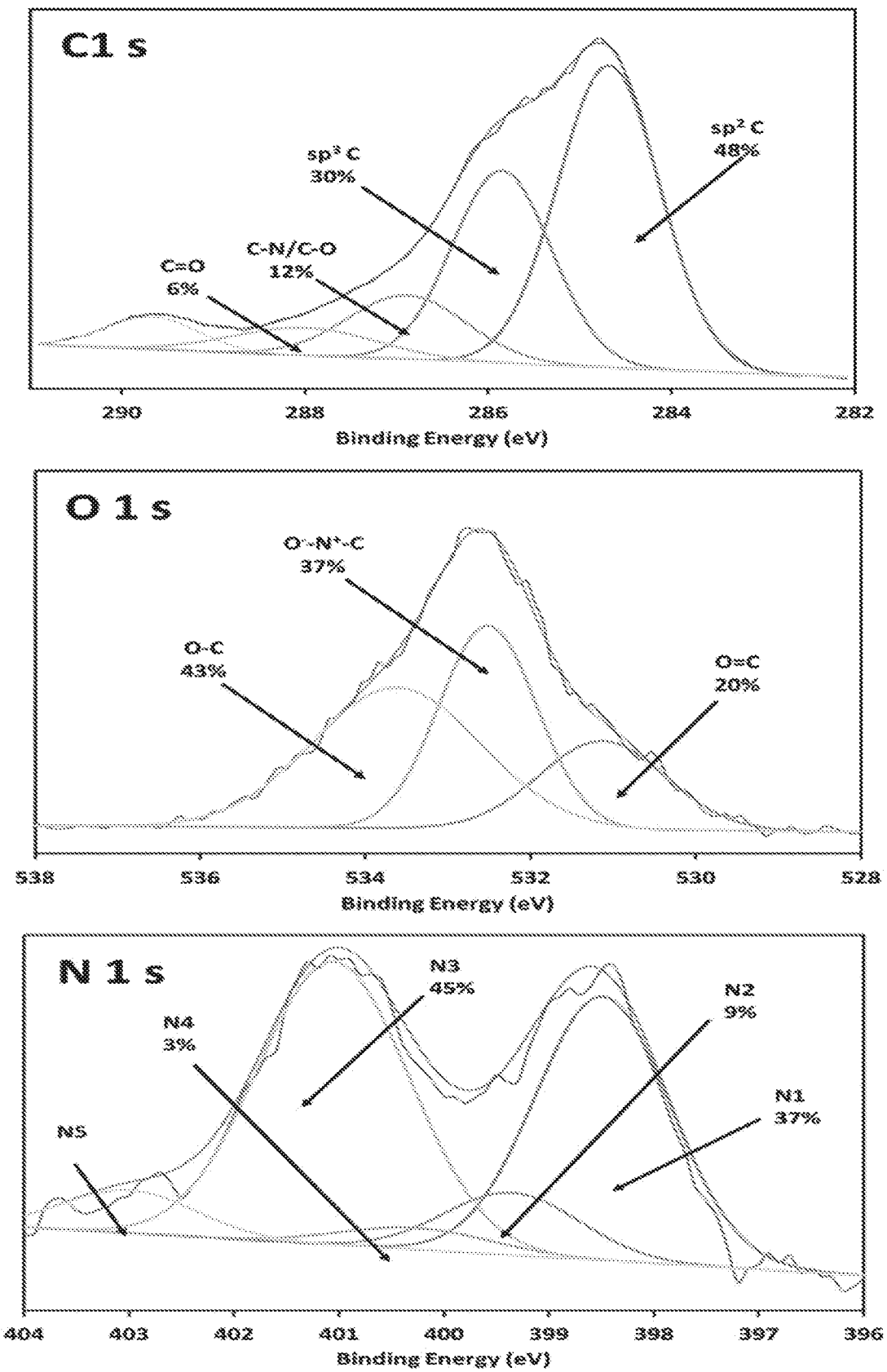
Figure 14:
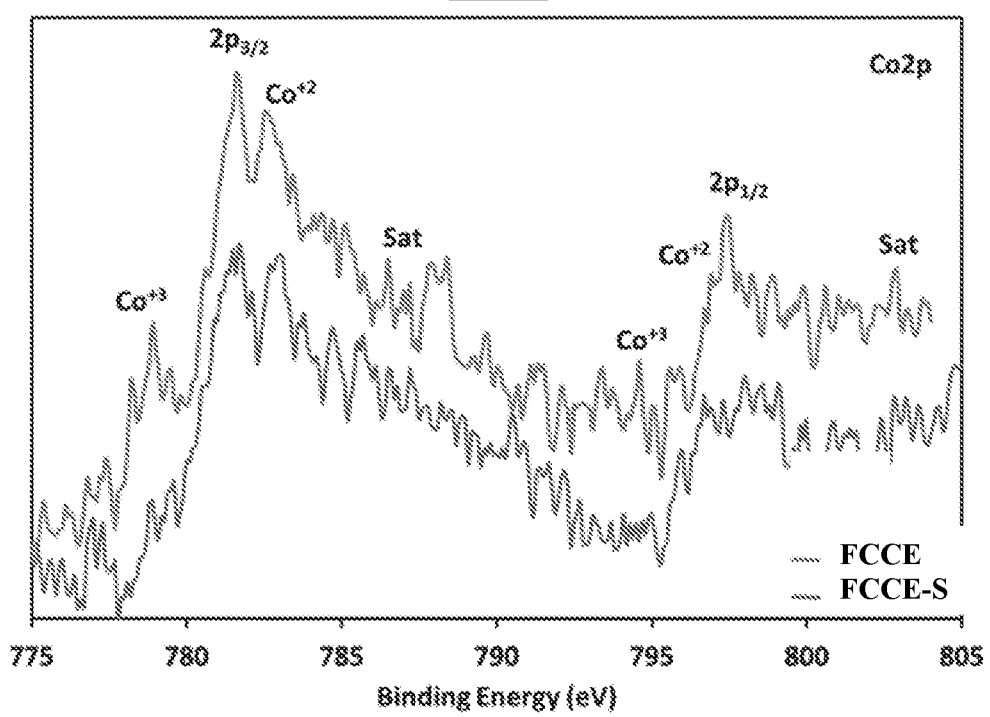
FIG. 14 illustrates XPS spectra for the Co2p transition from graphitic electrodes generated from fungal mats cultured with 10 mM $Co(NO_3)_2$ (FCCE) and heat-killed fungal mats soaked with $Co(NO_3)_2$.

X-Ray photoelectron spectroscopy (XPS) was performed on all of the graphitic materials to confirm the binding modes of nitrogen that could results from nitrate limitation and potential modes of binding between the FCCE and FCCE-S materials. The spectra for the cobalt oxygen binding is shown in FIG. 14, and the C, N, and O data for each material are shown in FIGS. 13A-13C. The analysis showed common peaks in the C1s, O1s, N1s spectra for all the materials. However, the bioaccumulation of Co during growth allowed for a different binding mode percentages. For 40-NO and FCCE-S materials, that were grown without Co, the C1s spectral features are dominated by aromatic carbons in both $sp^2$ (49%; 283.8 eV) and $sp^3$ (32%; 284.8 eV) with smaller concentrations of C—N/C—O (12%; 286.2 eV) and C=O (4%; 288.8 eV). High aromatic carbon abundances are traits indicative of condensation in the carbon structure and the development of a graphitic-like patterns. In a similar manner, the FCCE material had the majority of aromatic C binding but a much less intense $sp^2$ peak (19%), and higher C—N/C—O concentration (21%). The NO-40 and FCCE-S materials also shared similar peak intensities for the O1s spectrum with 43% O—C (533.2 eV), 37% O—N—C (532.0 eV), and 20% O=C (531.1 eV) oxygen binding modes, while FCCE was primarily dominated by O—C (52%). Without wishing to be limited by any theory, the contribution to increased $sp^3$ (50%) and C—N/C—O can be attributed to the higher Co and lower C concentrations, determined by EA, for the FCCE compared to both NO-40 and FCCE-S. For the N1s spectrum, all three materials were primarily composed of pyridinic (398.7 eV) and pyrrolic (401.1 eV) aromatic N bonding which is create a more conductive carbon material. The major difference from the Co grown sample was a 10% increase in pyridinic N bonding compared to NO-40 and FCCE-S.

Example 6: Use of Carbonaceous Electrodes in Solid Electrolyte Batteries

The fungal derived electrodes of the invention can also be used in "next generation" batteries which use solid ceramic electrolytes.

Figure 15:
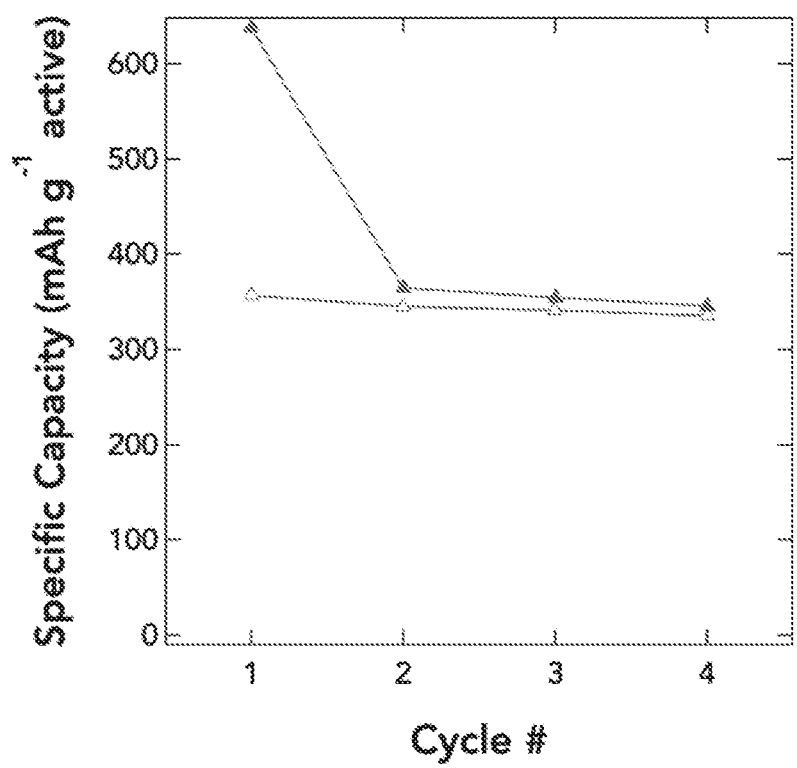
FIG. 15 comprises a graph of the specific capacity of the fungal derived material carbonized at 1000° C. used in a solid-state cell after a 1M KOH wash. The fungus was blended with a 77.5 solid electrolyte in 1:1 wt ratio. Rate of C/10 was used. Voltage window of 0.005-1V vs. Li+/Li.

Ground fungus which had been washed with 1M KOH and pyrolyzed at a maximum temperature of 1000° C. was blended with solid electrolyte (1:1) to produce a solid-state electrode. The solid electrolyte used was $77.5Li_2S-22.5P_2S_5$ glass (a77.5). The fungus was introduced at 50% mass loading, using no conductive additives. At rate C/10 with a voltage window of 0.005-1V vs. $Li^+/Li$, it was observed that the solid state cell achieved a capacity close to graphite (FIG. 15).

Figure 16:
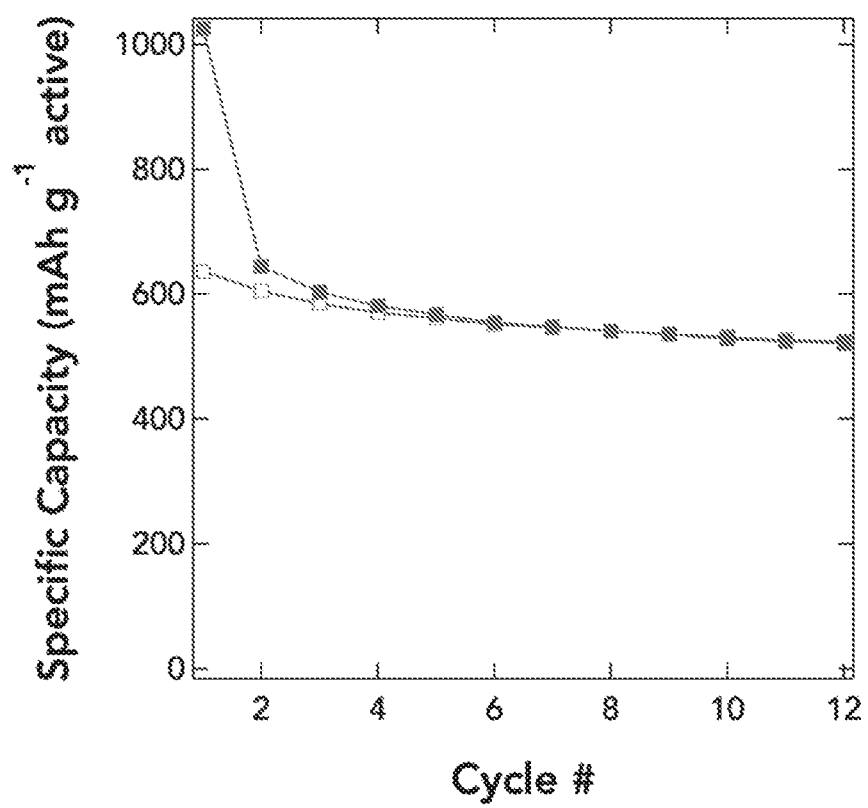
FIG. 16 comprises a graph of the specific capacity of the fungal derived material grown in the presence of 5 mg of nano-silicon, carbonized at 1000° C. used in a solid-state cell after a 1% HCl wash. The material was blended with a 77.5 solid electrolyte in 1:1 wt ratio. Rate of C/10 was used. Voltage window of 0.005-1V vs. Li+/Li.

The integration of battery materials was also tested by integrating silicon into the fungal material. 5 mg of nanosilicon was added into the growth medium of the filamentous fungus. By SEM, it was observed that the silicon was fully encapsulated by the fungus. With an otherwise identical set up to that described above, the silicon doped material showed increased capacity, well above graphite (FIG. 16). The material also demonstrated improved stability over the undoped material.

Figure 17:
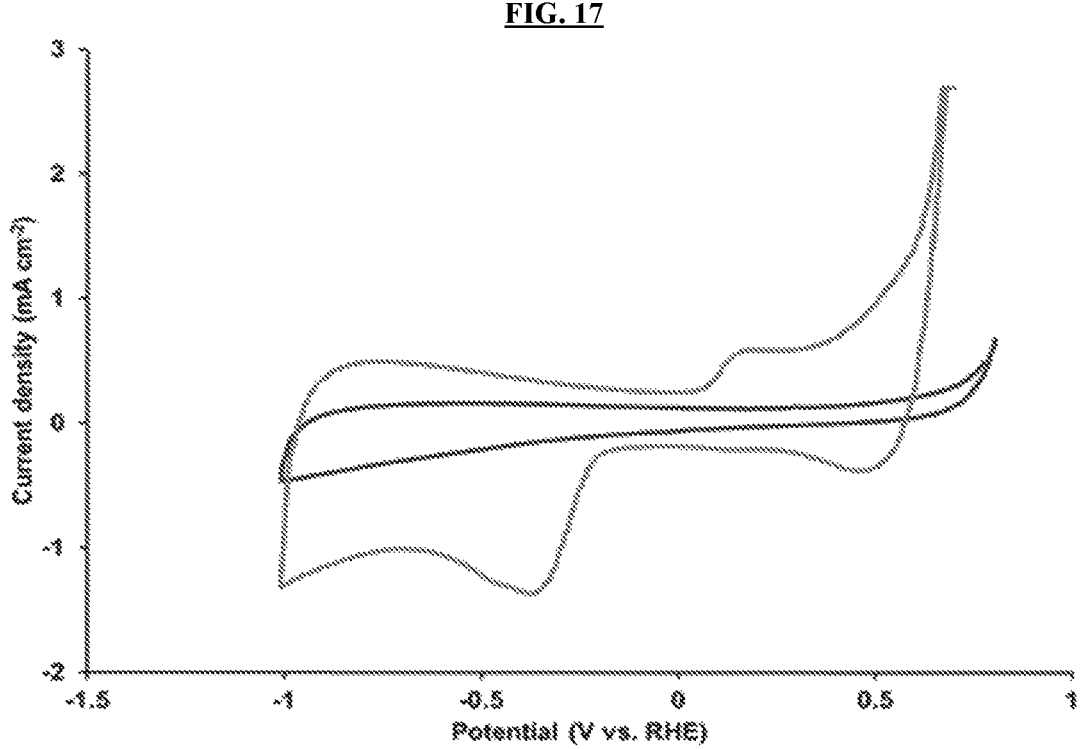
FIG. 17 is a graph illustrating cyclic voltammetry experiments for FCCE (higher peak density trace) and NO-40 (lower peak density trace) electrodes in 0.1 M NaOH under nitrogen at 25° C. normalized to the surface area of electrode (10 mV/s).

Example 7: Electrochemical Activity of Biotemplated Graphitic Monoliths Grown or Soaked with Cobalt Nitrate Solutions The free standing binder-less electrodes that resulted from pyrolysis were evaluated as an electrode material without any further post-processing. This was possible because a titanium (Ti) wire could be inserted into the lyophilized biomass prior to pyrolysis and the wire integrity was not compromised. This allowed for the graphitic disc to act as an electrode without the addition of chemical binders (FIG. 6C). The stability and electrochemical properties of fungal mats grown with Co and without cobalt were determined using cyclic voltammetry. Cyclic voltammetry was performed using the FCCE and NO-40 electrodes as the working electrode in 0.1 M KOH with repetitive cycles (FIG. 17). These experiments show that the cobalt containing electrodes were stable and did not lose activity after 50 potential sweeps between −1.0 and 0.6 V vs. Ag/AgCl at 10 mV $s^{-1}$. Irreversible oxidation peaks were observed for cobalt oxidation at 0.23 V vs. Ag/AgCl when compared to NO-40. This electrochemical stability was also observed in the opposite sweep direction.

Figure 18:
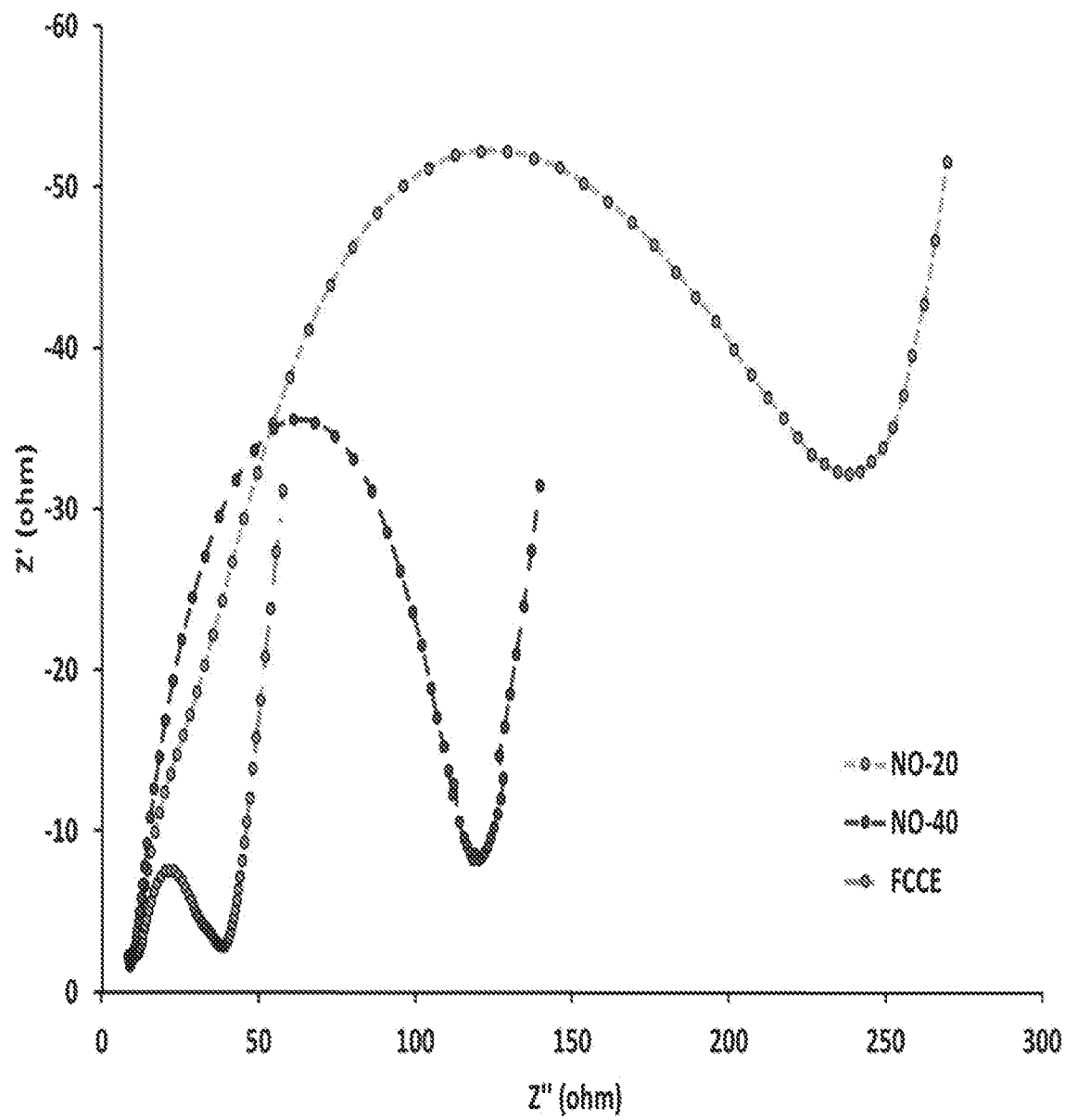
FIG. 18 illustrates electrochemical impedance spectra of graphitic electrodes generated from *N. crassa* cultured with 10 mM $Co(NO_3)_2$ (FCCE), 40 mM $NaNO_3$ (40-NO), or 20 mM $NaNO_3$ (20-NO).

To better understand the effects of growth conditions, the impedance of several electrodes were tested based on their chemical composition. Electrochemical impedance spectroscopy (EIS) is a tool that allows one to determine the heterogeneous charge-transfer properties of porous carbon materials. The Nyquist plots for electrodes created from *N. crassa* cultured with $Co(NO_3)_2$ [FCCE] and cultured with either 20 mM or 40 mM $NaNO_3$ (NO-20 and NO-40, respectively) are shown in FIG. 18. These materials were chosen as electrodes due to the differences in the C/N ratio (Table 1) and incorporation of $Co(NO_3)_2$ into the structure. Each of the materials tested showed a clear high frequency semicircle followed by a straight near vertical line in the low frequency region. The semicircle is generally associated with the charge transfer resistance while the sloped line is related to the Warburg impedance of Li-ion diffusion. Comparison of the impedance spectra from FCCE to the nitrate cultured materials revealed a 55±3% increase in charge transfer resistance to the NO-40 electrode and an 81±3% increase for NO-20. The initial difference between the cobalt containing structure and NO-20 and NO-40 can be explained by increased metal conductivity. The difference in the charge transfer resistance between the NO-20 and NO-40 can be attributed to the difference in the C/N ratio. The slope of the line in the low frequency region is similar for each material, an indication a similarity in porosity and ion diffusion.

Figure 19:
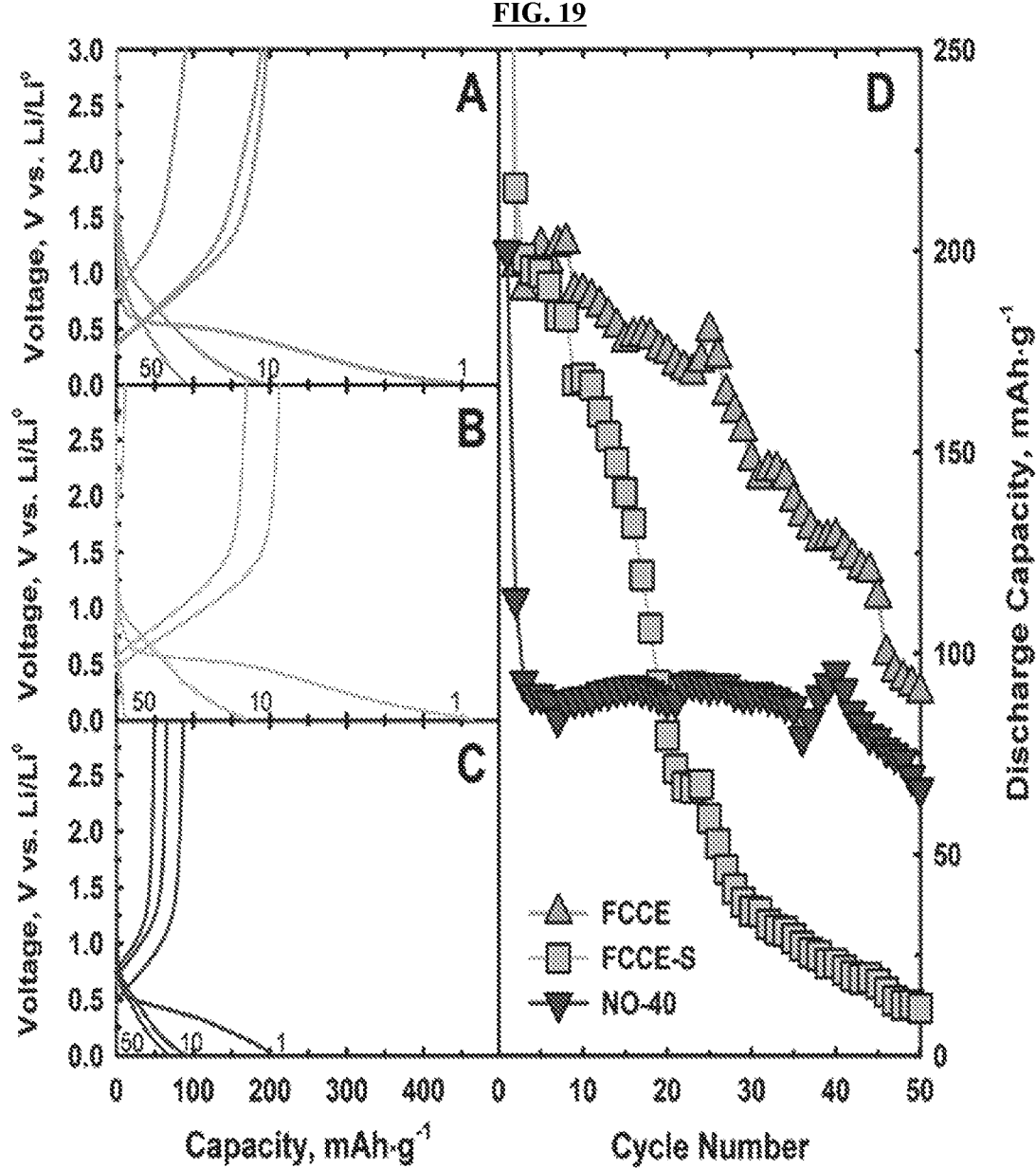
FIG. 19 illustrates cycling curves and capacity retention for *N. crassa* graphitic electrodes cultured with 10 mM $Co(NO_3)_2$ (FCCE), heat-killed *N. crassa* soaked with 10 mM $Co(NO_3)_2$ (FCCE-S), and *N. crassa* grown with 40 mM $NaNO_3$ (NO-40). Galvanostatic charge/discharge cycles of A) 2 Co, B) Co SOAK, and C) C ONLY in 1 M $LiPF_6$ in 1/1 v/v, ethylene carbonate/ethylmethyl carbonate. D) Capacity retention for the same cells shown in A-C.

The galvanostatic charge/discharge (CD) behavior of electrodes generated from the growth of *N. crassa* with $Co(NO_3)_2$ [FCCE] and fungal mats soaked with $Co(NO_3)_2$ [FCCE-S] were compared to electrode generate from growth with 40 mM sodium nitrate (NO-40) (FIG. 19). In the first discharge the capacities of FCCE, FCCE-S, and NO-40 were 450, 452, and 200 mA h $g^{-1}$ with the subsequent cycles resulting in loss of this initial capacity immediately. The NO-40 electrode did stabilize at a discharge capacity between 75-50 mA h $g^{-1}$ until the 50th cycle. The comparison between the electrodes that were grown with cobalt nitrate versus soaked with cobalt nitrate showed very different discharge behavior. The FCCE electrode stabilized at 200 mA h $g^{-1}$ and gradually decreased in capacity to 98 mA h $g^{-1}$ after 50 cycles while FCCE-S showed the same discharge behavior as FCCE for the first 10 cycles but this capacity dropped off rapidly to below 40 mA h g'. This charge discharge behavior confirms that growing the fungal mat exposed to cobalt creates a better electrochemical material than soaking the fungal mat in cobalt and that the materials created by culturing the fungus exposed to the metal will ultimately lead to a better battery material for lithium.

Example 8: Use of Carbonaceous Electrodes in Liquid Li-Ion Batteries

Figure 20:
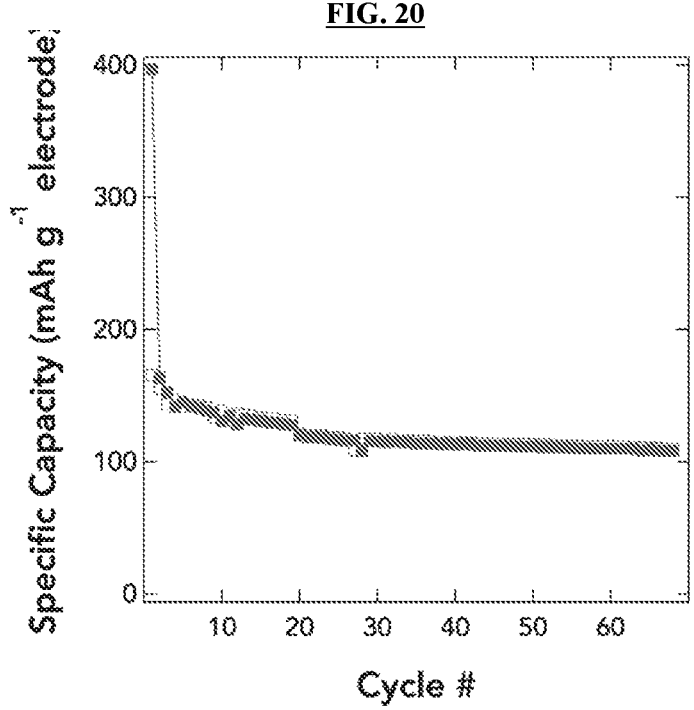
FIG. 20 is an illustrative graph of the specific capacity of a fungal derived material carbonized at 800° C. for 2 hours and ground and used in an electrode in a liquid-based lithium ion battery (1:1 EC:DEC 1M $LiPF_6$). Fungus:binder (PVDF) 80:20 wt, counter electrode is lithium foil; C/20 formation cycle, C/10 up to 20 cycles, C/5 for remaining cycles. Voltage window of 0.05-1V vs. Li+/Li.

Fungal material grown in the absence of any inorganic salt additives was ground and used in an electrode in a liquid-based lithium ion battery (FIG. 20) (1:1 EC:DEC 1M $LiPF_6$). The mass loading of these cells was 80:20 active material:polyvinylidene fluoride (PVDF), a common polymeric binder. The material was carbonized at 800° C. yielding a soft carbon. The soft carbon accounts for much of the first cycle irreversibility. A rate as high as C/5 was demonstrated. Due to the high electrical conductivity of the active material, and desirable structure, no conductive additive was needed.

Figure 21:
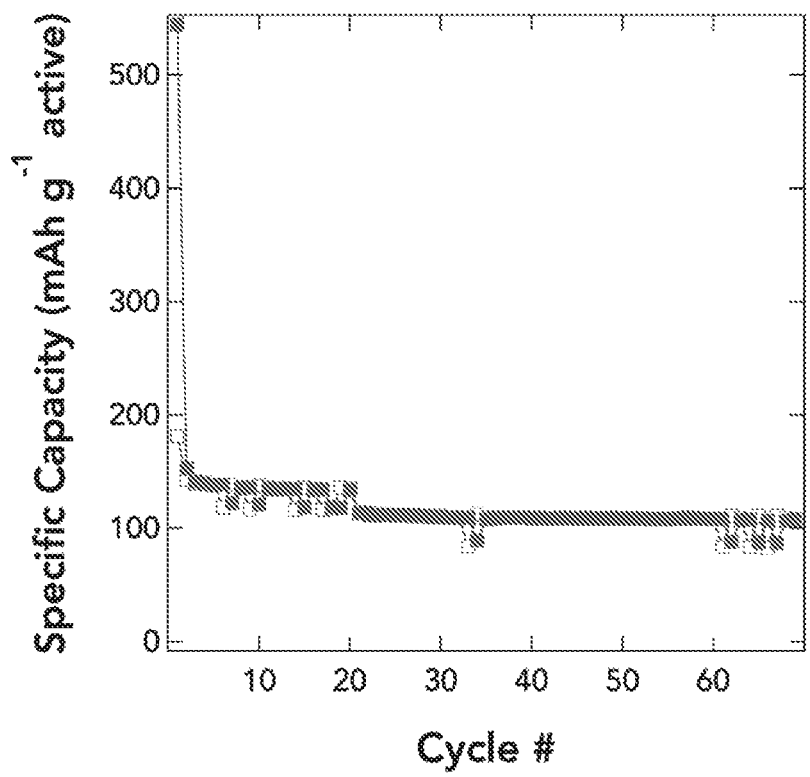
FIG. 21 is an illustrative graph of the specific capacity of "as-grown" fungus carbonized at 800° C. for 2 hours and used in an electrode in a liquid-based lithium ion battery (1:1 EC:DEC 1M $LiPF_6$). No binder was added to the electrode, counter electrode is lithium foil; C/20 formation cycle, C/10 up to 20 cycles, C/5 for remaining cycles. Voltage window of 0.05-1V vs. Li+/Li. The unground material demonstrates enhanced capacity over the capacity of the ground material reported in FIGS. 8A-8B.

A fungal electrode was also used "as-is" in a lithium-ion cell with organic liquid electrolyte after being carbonized at 800° C. for two hours (FIG. 21). High stability was observed even at high rates. Low first cycle efficiency was observed, however, this particular electrode did not employ any washes. The as-grown system does not require any binder or conductive additive boosting the overall electrode based capacity as it has not been ground down. Typical lithium-ion graphite electrodes only contain 90% active material, whereas, the grown fungus electrode when used "as-is" consists of 100% active material, providing a 10% increase in base capacity. The binderless aspect of the material also avoids much of the hazardous preparation methods common for making lithium-ion electrodes.

Figure 22:
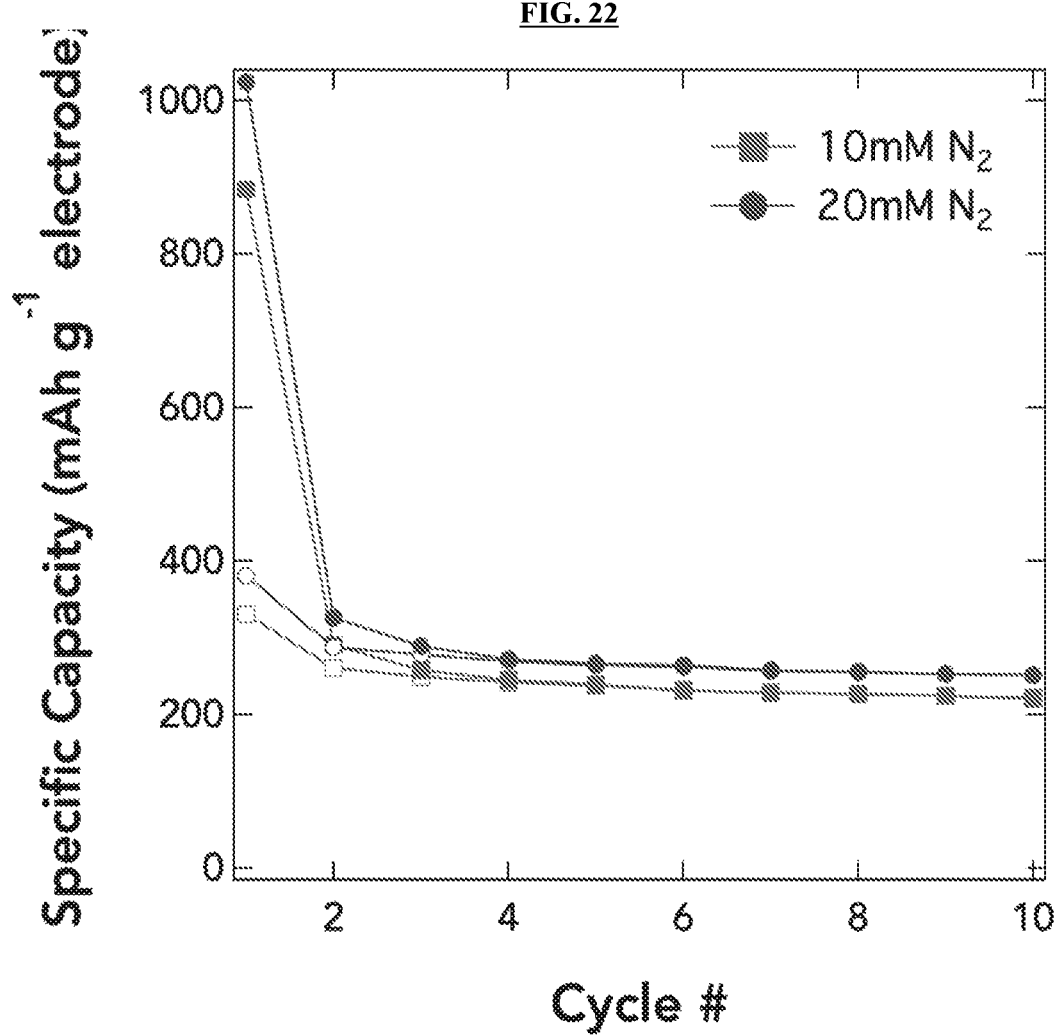
FIG. 22 is an illustrative graph of the specific capacity of "as-grown" fungal derived material, grown under varied $N_2$ concentrations, carbonized at 800° C. for 2 hours and used in an electrode in a liquid-based lithium ion battery (1:1 EC:DEC 1M $LiPF_6$) after a 1% HCl wash. No binder was added to the electrode, the counter electrode is lithium foil; C/20 formation cycle, C/10 up to 20 cycles, C/5 for remaining cycles. Voltage window of 0.05-1V vs. Li+/Li. The HCl washed material demonstrates enhanced capacity over the capacity of the unwashed, ground material reported in FIG. 20.

A set of fungal electrode was tested "as-is" in a lithium-ion cell with organic liquid electrolyte after being carbonized at 800° C. for two hours under different atmospheric conditions (FIG. 22). One electrode was carbonized under a 10 mM $N_2$ atmosphere while the other was carbonized under a 20 mM $N_2$ atmosphere. Both electrodes were washed with 1% HCl prior to use, reducing biomass impurities down to less than 1%. The stable capacity was much improved by the acid wash as compared to other electrodes that had not been washed. Overall, improvement was observed for these electrodes over the ground, unwashed, undoped electrodes reported elsewhere herein.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A carbonaceous material comprising a graphitic, partially graphitic, or amorphous carbon matrix, wherein the carbon matrix comprises a plurality of fibers,
    wherein each one of the plurality of fibers independently has a diameter ranging from about 0.1 μm to about 100 μm and is in physical contact with at least one other of the plurality of fibers;
    wherein the carbon matrix has a surface area ranging from about 1 $m^2$ $g^{-1}$ to about 3,000 $m^2$ $g^{-1}$; and
    wherein the carbon matrix comprises a plurality of pores that are present throughout the carbon matrix, wherein each one of the plurality of pores independently has a diameter ranging from about 0.1 μm to about 1 cm and is in fluid connection with at least one other of the plurality of pores.

2. The carbonaceous material of claim 1, which is prepared by carbonizing a filamentous organism optionally grown in the presence of at least one organic or inorganic compound wherein, if present, at least a portion of the at least one organic or inorganic compound is within or on the surface of the carbon matrix.

3. The carbonaceous material of claim 2, wherein the filamentous organism is at least one selected from the group consisting of a filamentous algae, filamentous fungus and filamentous bacterium.

4. The carbonaceous material of claim 2, wherein the filamentous organism is wild type or genetically modified *Neurospora crassa*.

5. The carbonaceous material of claim 2, wherein at least one applies: (a) the filamentous organism is carbonized by heating to a maximum temperature of about 100° C. to about 2,500° C.; (b) the filamentous organism is heated from room temperature to the maximum temperature at a rate of about 1° C./min to about 100° C./min; (c) the filamentous organism is heated at the maximum temperature for about 1 hours to 100 hours; (d) the filamentous organism is heated in the presence of a gas with a flow rate between about 1 mL/min and about 1000 mL/min; (e) the filamentous organism is heated in a vacuum.

6. The carbonaceous material of claim 1, wherein at least one of the plurality of fibers (a) is not physically bound to any of the others of the plurality of fibers, or (b) is physically bound to at least one other of the plurality of fibers.

7. The carbonaceous material of claim 1, wherein at least one of the plurality of fibers is physically bound to a first other of the plurality of fibers through a first branching point and physically bound to a second other of the plurality of fibers through a second branching point, wherein the separation of the first and second branching points along the length of the at least one of the plurality of fibers ranges from about 0.1 μm to about 1000 μm.

8. The carbonaceous material of claim 1, wherein the carbon matrix further comprises at least one organic or inorganic compound that is within or on the surface of at least a fraction of the plurality of fibers and is present throughout the carbon matrix.

9. The carbonaceous material of claim 8, wherein at least one applies: (a) the at least one inorganic compound is selected from the group consisting of transition metal salts, alkali metal salts, alkaline earth metal salts, nitrate salts, sulfate salts, phosphate salts, metal particles, metalloid particles, metal oxides; (b) the at least one inorganic compound is selected from the group consisting of cobalt nitrate, sodium nitrate, magnesium sulfate and silicon nanoparticles.

10. The carbonaceous material of claim 1, wherein each one of the plurality of pores independently has a diameter ranging from about 1 μm to about 10 mm.

11. The carbonaceous material of claim 1, wherein at least one applies: (a) the material further comprises comprising a compound selected from silicon nanoparticles, silicon oxide nanoparticles and $Co_2O_3$ nanoparticles; (b) the material is suitable for use as an electrode; (c) the material is suitable for use as an electrode in a solid state battery or a lithium-ion battery.

12. A battery device comprising the carbonaceous material of claim 1 and a lithium-containing electrolyte.

* * * * *